United States Patent
Scheiner et al.

(10) Patent No.: US 11,839,407 B2
(45) Date of Patent: Dec. 12, 2023

(54) TREATMENT OF OBSTRUCTIVE SLEEP APNEA (OSA)

(71) Applicant: Medtronic Xomed, Inc., Jacksonville, FL (US)

(72) Inventors: Avram Scheiner, Vadnais Heights, MN (US); James Hissong, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 17/815,463

(22) Filed: Jul. 27, 2022

(65) Prior Publication Data

US 2022/0361916 A1 Nov. 17, 2022

Related U.S. Application Data

(62) Division of application No. 16/752,023, filed on Jan. 24, 2020, now Pat. No. 11,426,201.

(51) Int. Cl.
*A61B 17/34* (2006.01)
*A61N 1/05* (2006.01)
*A61B 17/00* (2006.01)

(52) U.S. Cl.
CPC ...... *A61B 17/3468* (2013.01); *A61B 17/3403* (2013.01); *A61N 1/0548* (2013.01); *A61B 2017/00929* (2013.01)

(58) Field of Classification Search
CPC ............ A61B 17/3403; A61B 17/3468; A61B 5/4809; A61B 5/4815; A61B 5/4812; A61B 5/682; A61B 5/566; A61B 5/4818; A61B 5/296; A61B 5/686; A61N 1/0548; A61M 2205/3303
See application file for complete search history.

(56) References Cited

U.S. PATENT DOCUMENTS 4,886,065 A 12/1989 Collins, Jr. et al.
5,146,918 A 9/1992 Kallok et al.
(Continued)

FOREIGN PATENT DOCUMENTS

EP 0972538 A2 1/2000
EP 3071288 B1 11/2018
(Continued)

OTHER PUBLICATIONS

International Preliminary Report on Patentability from International Application No. PCT/US2021/014689 dated Aug. 4, 2022, 9 pp.
(Continued)

*Primary Examiner* — Majid Jamialahmadi
(74) *Attorney, Agent, or Firm* — Shumaker & Sieffert, P.A.

(57) ABSTRACT

A system for treatment of obstructive sleep apnea (OSA) is described. The system includes an introducer needle having an elongated body. The introducer needle is configured to create an opening in a tongue of a patient for implantation of a lead for treating OSA. One or more electrically conductive areas are located on the elongated body. A medical device is configured to deliver a stimulation signal via the introducer needle through the one or more electrically conductive areas to the tongue of the patient to stimulate one or more motor points of a protrusor muscle within the tongue of the patient.

3 Claims, 10 Drawing Sheets

(56) References Cited

U.S. PATENT DOCUMENTS

| | | | |
|---|---|---|---|
| 5,540,733 | A | 7/1996 | Testerman et al. |
| 5,546,952 | A | 8/1996 | Erickson |
| 5,549,655 | A | 8/1996 | Erikcson |
| 5,591,216 | A | 1/1997 | Testerman et al. |
| 6,044,297 | A | 3/2000 | Sheldon et al. |
| 6,269,269 | B1 | 7/2001 | Ottenhoff et al. |
| 6,345,202 | B2 | 2/2002 | Richmond et al. |
| 7,845,357 | B2 | 12/2010 | Buscemi et al. |
| 8,366,615 | B2 | 2/2013 | Razavi |
| 8,588,941 | B2 | 11/2013 | Mashiach |
| 8,744,589 | B2 | 6/2014 | Bolea et al. |
| 8,751,005 | B2 | 6/2014 | Meadows et al. |
| 8,813,753 | B2 | 8/2014 | Bhat et al. |
| 8,909,341 | B2 | 12/2014 | Gelfand et al. |
| 9,486,628 | B2 | 11/2016 | Christopherson et al. |
| 9,643,004 | B2 | 5/2017 | Gerber |
| 9,662,045 | B2 | 5/2017 | Skelton et al. |
| 9,662,497 | B2 | 5/2017 | Meadows et al. |
| 9,757,560 | B2 | 9/2017 | Papay |
| 9,849,289 | B2 | 12/2017 | Mashiach et al. |
| 9,884,191 | B2 | 2/2018 | Meadows et al. |
| 9,888,864 | B2 | 2/2018 | Rondoni et al. |
| 9,889,299 | B2 | 2/2018 | Ni et al. |
| 9,895,541 | B2 | 2/2018 | Meadows et al. |
| 10,029,098 | B2 | 7/2018 | Papay |
| 10,065,038 | B2 | 9/2018 | Papay |
| 10,195,428 | B2 | 2/2019 | Scheiner |
| 10,744,339 | B2 | 8/2020 | Makansi |
| 2002/0049479 | A1 | 4/2002 | Pitts |
| 2003/0216789 | A1 | 11/2003 | Deem et al. |
| 2007/0123950 | A1 | 5/2007 | Ludlow et al. |
| 2007/0173893 | A1 | 7/2007 | Pitts |
| 2008/0103407 | A1 | 5/2008 | Bolea et al. |
| 2008/0161874 | A1 | 7/2008 | Bennett et al. |
| 2009/0270962 | A1 | 10/2009 | Yang et al. |
| 2011/0270339 | A1 | 11/2011 | Murray, III et al. |
| 2011/0270340 | A1 | 11/2011 | Pellegrini et al. |
| 2012/0089153 | A1 | 4/2012 | Christopherson et al. |
| 2013/0253309 | A1 | 9/2013 | Allan et al. |
| 2013/0253342 | A1 | 9/2013 | Griswold et al. |
| 2013/0253343 | A1 | 9/2013 | Waldhauser et al. |
| 2013/0253344 | A1 | 9/2013 | Griswold et al. |
| 2013/0253345 | A1 | 9/2013 | Griswold et al. |
| 2013/0253346 | A1 | 9/2013 | Griswold et al. |
| 2013/0253347 | A1 | 9/2013 | Griswold et al. |
| 2014/0031891 | A1 | 1/2014 | Mashiach |
| 2014/0135868 | A1 | 5/2014 | Bashyam |
| 2014/0228905 | A1 | 8/2014 | Bolea |
| 2014/0323839 | A1 | 10/2014 | MCCreery |
| 2015/0100106 | A1 | 4/2015 | Shishilla et al. |
| 2017/0087360 | A1* | 3/2017 | Scheiner ............ A61N 1/36139 |
| 2017/0151432 | A1 | 6/2017 | Christopherson et al. |
| 2017/0340891 | A1 | 11/2017 | Boggs et al. |
| 2018/0117316 | A1 | 5/2018 | Wagner et al. |
| 2020/0269044 | A1 | 8/2020 | Papay |
| 2020/0281763 | A1 | 9/2020 | Scheiner |
| 2020/0338358 | A1 | 10/2020 | Makansi |
| 2020/0346017 | A1 | 11/2020 | Caparso et al. |
| 2021/0228234 | A1 | 7/2021 | Scheiner et al. |

FOREIGN PATENT DOCUMENTS

| | | |
|---|---|---|
| GB | 2320193 A | 6/1998 |
| WO | 03/084398 A1 | 10/2003 |
| WO | 03/105668 A2 | 12/2003 |
| WO | 2010/117810 A1 | 10/2010 |
| WO | 2017087681 A1 | 5/2017 |

OTHER PUBLICATIONS

Gharb et al., "Microsurgical Anatomy of the Terminal Hypoglossal Nerve Relevant for Neurostimulation in Obstructive Sleep Apnea," Neuromodulation: Technology at the Neural Interface, Aug. 5, 2015, 8 pp.

Heiser et al., "Surgical anatomy of the hypoglossal nerve: a new classification system for selective upper airway stimulation," Wiley Online, May 22, 2017, 10 pp.

International Search Report and Written Opinion of International Application No. PCT/US2021/014689, dated May 6, 2021, 15 pp.

Medtronic, "Basic Evaluation Procedure Technique Without Fluoroscopy—Part 3: Needle Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 4: Test Lead Placement," Training Video accessed from https://www.medtronic.com/us-en/healthcare-professionals/therapies-procedures/urology/sacral-neuromodulation/education-training/videos.html, webpage last updated Feb. 2018, 8 pp.

Medtronic, "Basic Evaluation Procedure Technique Without Fluoroscopy—Part 5: Securing & Connecting Test Leads," Training Video accessed from https://www.medtronic.com/us-en/healthcare-professionals/therapies-procedures/urology/sacral-neuromodulation/education-training/videos.html, webpage last updated Feb. 2018, 8 pp.

Mu et al., "Human Tongue Neuroanatomy: Nerve Supply and Motor Endplates," Oct. 2010, accessed from NIH Public Access, 27 pp.

Prosecution History from U.S. Appl. No. 16/752,023, dated May 27, 2021 through Apr. 29, 2022, 39 pp.

U.S. Appl. No. 62/814,398, naming inventor Avram Scheiner, filed Mar. 6, 2019.

* cited by examiner

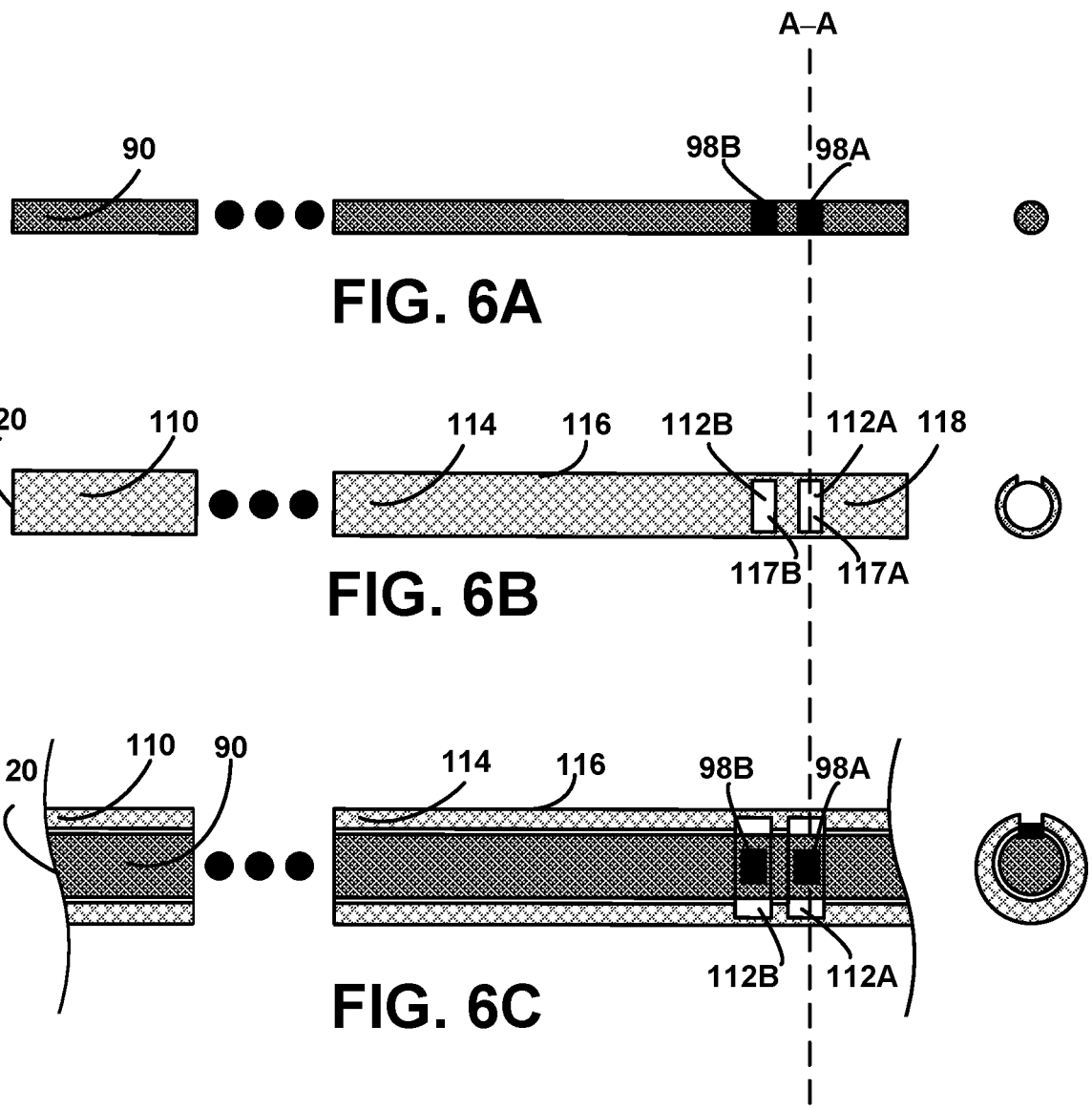

TREATMENT OF OBSTRUCTIVE SLEEP APNEA (OSA)

This application is a divisional of U.S. patent application Ser. No. 16/752,023, filed Jan. 24, 2020, the entire content of which is incorporated herein by reference.

TECHNICAL FIELD

This disclosure relates to medical device systems and, more particularly, to medical device systems for delivery of electrical stimulation therapy.

BACKGROUND

Obstructive sleep apnea (OSA), which encompasses apnea and hypopnea, is a disorder in which breathing may be irregularly and repeatedly stopped and started during sleep, resulting in disrupted sleep and reduced blood oxygen levels. Muscles in a patient's throat intermittently relax thereby allowing soft tissues of the throat to obstruct the upper airway while sleeping and cause OSA. In patients with a smaller than normal airway, airflow into the upper airway can be obstructed by the tongue or soft pallet moving to the back of the throat and covering the airway. Loss of air flow also causes unusual inter-thoracic pressure as a person tries to breathe with a blocked airway. Lack of adequate levels of oxygen during sleep can contribute to abnormal heart rhythms, heart attack, heart failure, high blood pressure, stroke, memory problems, and increased accidents during the day due to inadequate sleep. Additionally, loss of sleep occurs when a person is awakened during an apneic episode.

SUMMARY

The devices, systems, and techniques of this disclosure generally relate to an implantable medical device (IMD) system and methods for therapy for obstructive sleep apnea (OSA) but can be extended to address other patient symptoms and disorders. With OSA, a patient's tongue may relax during sleep and block the patient's airway. Some example techniques to address OSA include electrically stimulating one or both hypoglossal nerves and/or motor points in the tongue of the patient. In response to the electrical stimulation, the hypoglossal nerve(s) causes protrusor muscles (e.g., genioglossus and geniohyoid muscles) to contract and move the tongue forward, thereby opening the airway. In some examples, in response to stimulating at the motor points of the protrusor muscles (e.g., a location where an axon of the hypoglossal nerve terminates at a muscle fiber), the protrusor muscles may contract to move the tongue forward, thereby opening the airway.

To stimulate the hypoglossal nerve(s) and/or motor points, a medical device outputs electrical stimulation therapy via one or more electrodes on one or more implanted leads to cause the tongue to move forward. A medical professional can implant the one or more leads into the tongue of the patient. The one or more implanted leads each include one or more electrodes coupled to the medical device (e.g., an implantable or external medical device that delivers electrical stimulation via one or more electrodes on the lead).

With lead placement in the tongue, there may be issues related to how and where to place a lead to provide effective therapy. This disclosure describes example techniques for lead structures and/or lead placement that may overcome one or more issues. Although the example techniques are described with respect to lead placement in the tongue for treating OSA, the example techniques should not be considered to be limited to lead placement in the tongue or limited to treating OSA.

In an example, the disclosure describes a system for treatment of OSA. The system includes an introducer needle having an elongated body. The introducer needle is configured to create an opening in a tongue of a patient for implantation of a lead for treating OSA. One or more electrically conductive areas are located on the elongated body. A medical device is configured to deliver a stimulation signal via the introducer needle through the one or more electrically conductive areas to the tongue of the patient to stimulate one or more motor points of a protrusor muscle within the tongue of the patient.

In an example, the disclosure describes a system for treatment of OSA. The system includes an introducer needle having an elongated body. The introducer needle is configured to create an opening in a tongue of a patent for implantation of a lead for treating OSA. One or more electrically conductive areas are located on the elongated body. An introducer sheath is able to be placed within the opening created by the introducer needle. The introducer sheath may have one or more perforations that align with one or more electrodes of the lead inserted into the introducer sheath. One or more medical devices are configured to deliver a stimulation signal via the introducer needle through the one or more electrically conductive areas to the tongue of the patient to stimulate one or more motor points of a protrusor muscle within the tongue of the patient. The one or more medical devices are further configured to deliver the stimulation signal with the one or more electrodes of the lead that is inserted into the introducer sheath and through the one or more perforations of the introducer sheath to the tongue of the patient.

In one example, the disclosure describes a method for treatment of OSA. The method includes inserting an introducer needle through tissue near a chin of a patient and through a tongue of the patient to create an opening in a tongue of a patent for implantation of a lead for treating OSA. The introducer needle has an elongated body. One or more electrically conductive areas are located on the elongated body. The method further includes controlling a medical device to deliver a stimulation signal via the introducer needle through the one or more electrically conductive areas to the tongue of the patient to stimulate one or more motor points of a protrusor muscle within the tongue of the patient.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 6A-6C are conceptual diagrams illustrating a lead and an example introducer needle which may be utilized in the system of FIG. 1.

DETAILED DESCRIPTION

Figure 1:
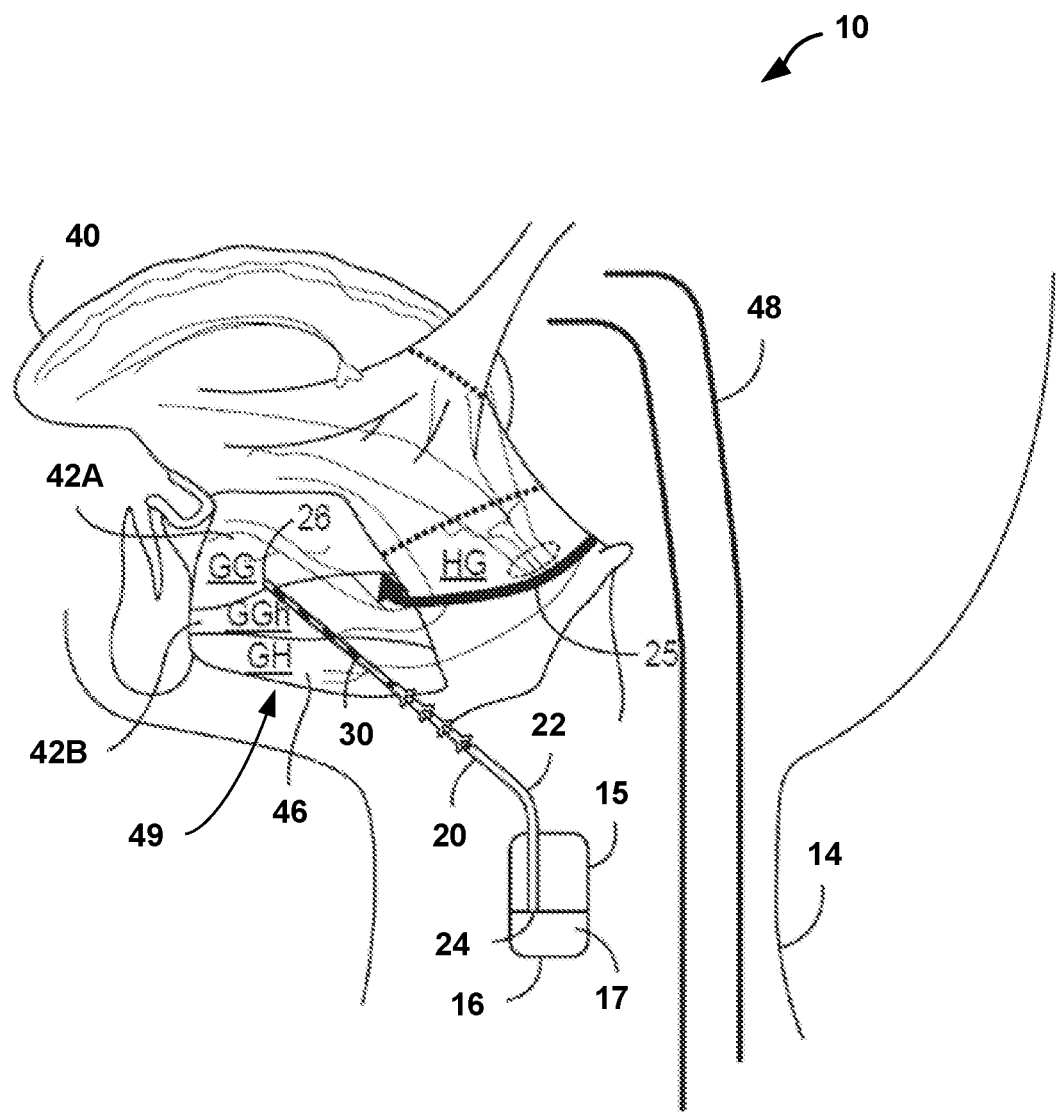
FIG. 1 is a conceptual diagram of an implantable medical device (IMD) system for delivering obstructive sleep apnea (OSA) therapy.

Medical devices, systems, and techniques for delivering electrical stimulation to the protrusor muscles of the tongue for the treatment of obstructive sleep apnea (OSA) are described in this disclosure. Electrical stimulation is delivered to cause the tongue of a patient to enter a protruded state, during sleep, to avoid or reduce upper airway obstruction. As used herein, the term, "protruded state" with regard to the tongue refers to a position that is moved forward and/or downward compared to a non-stimulated position or a relaxed position of the tongue. The protruded state is a state associated with contraction (e.g., via innervation from nerves in response to electrical stimulation) of protrusor muscles of the tongue (also sometimes referred to as "protruder" muscles of the tongue) including the genioglossus and geniohyoid muscles. A protruded state may be the opposite of a retracted and/or elevated position associated with the contraction of the retractor muscles (e.g., styloglossus and hyoglossus muscles) which retract and elevate the tongue. Electrical stimulation is delivered to cause the tongue to move (e.g., by depolarizing the nerve(s) that innervate the genioglossus and/or geniohyoid muscles) to and maintain a protruded state. As discussed above, the protruded state may prevent collapse or blockage of, open, or widen the upper airway of a patient to at least partially maintain or increase airflow (e.g., promote unrestricted airflow or at least reduced restriction of airflow during breathing).

A surgeon implants one or more leads that each include one or electrodes into the tongue such that the electrodes are proximate to a hypoglossal nerve and/or motor points (e.g., one or more locations where axons of the hypoglossal nerve terminate at respective muscle fibers of the protrusor muscles). For example, there are two hypoglossal nerves in the tongue of the patient. In one example, one lead may be used to stimulate (e.g., by delivering electrical stimulation through one or more electrodes of the lead) one of the two hypoglossal nerves, one lead may be used to stimulate both hypoglossal nerves, or two leads may be used, where each lead stimulates a respective one of the hypoglossal nerves. Stimulation of either or both hypoglossal nerves of the tongue can cause contraction of the protrusor muscles to reduce the effect of or prevent OSA.

There are multiple sets of motor points for each of the protrusor muscles on the left side and the right side. Each motor point may innervate one or more muscle fibers of the protrusor muscle. In one example, one lead may be used to stimulate motor points for the protrusor muscles on one side of the tongue, one lead may be used to stimulate motor points for protrusor muscles on both sides of the tongue, or two leads may be used, where each lead stimulates a respective set of motor points for the protrusor muscles on each side. Stimulation of either or both sets of motor points of the tongue can cause contraction of the protrusor muscles to reduce the effect of, or prevent, OSA.

This disclosure describes examples of techniques related to implantation of the one or more leads in the tongue for treatment of OSA. Although the example techniques are described with respect to OSA, the example techniques should not be construed as limited to OSA. Rather, the example techniques described in this disclosure may be applicable to lead implantation for treatment of various conditions, including lead implantation for treatment of conditions where the lead is implanted in a location other than the tongue.

Open surgeries may be performed to implant the one or more leads in a tongue of a patient for treating OSA. However, such open surgeries require dissection of tissue to expose one or more hypoglossal nerves and/or motor points for placement of the one or more leads immediately adjacent to or around the hypoglossal nerves and/or motor points in the tongue of the patient, which is relatively invasive and time-consuming. This disclosure describes examples of implant systems and methods for implanting the one or more leads in the tongue of the patient in a manner that may reduce the invasiveness and duration of the surgeries.

As described in more detail, implant systems may include introducer needles and medical devices for determining a target treatment site in the tongue of the patient for implantation of the one or more leads. The example introducer needles described in this disclosure may include one or more electrically conductive areas, and the one or more electrically conductive areas may be used to deliver stimulation signals. Responsive to the delivery of the stimulation signals, a surgeon or other medical professional may visually inspect if there is movement of the protrusor muscles. However, in some examples, a medical device may be utilized to detect one or more electrical signals (e.g., electromyography (EMG) signals) that are generated in response to the delivery of the stimulation signals through the introducer needle to determine if there is activation of the protrusor muscles. The detection of one or more electrical signals may be in addition to or instead of visual inspection. The example medical devices described in this disclosure may be coupled with the example introducer needles, and may generate the stimulation signals, receive the one or more electrical signals detected by the introducer needles, and output information indicatives of the one or more electrical signals.

The example techniques described in this disclosure may enable a surgeon to implant one or more leads adjacent to or around one or more hypoglossal nerves and/or motor points in the tongue of a patient without dissecting tissue to expose the hypoglossal nerves and/or motor points, which minimize access incision, shorten recovery time for the patient, and reduce risk for misplacement of the leads. For example, by stimulating locations within the tongue with the introducer needle, the surgeon may determine an appropriate location for implantation of the lead before the implantation of the lead. Moreover, in some examples, the electrically conductive areas on the introducer needle may align with the electrodes of the lead (e.g., the spacing and shape of the electrically conductive areas on the introducer needle is same as spacing and shape of the electrodes on the lead). In such cases, the surgeon may be able to replicate the electrical field that will be generated by the lead post lead placement with the electrically conductive areas of the introducer needle to determine the efficacy of the treatment before lead placement.

FIG. 1 is a conceptual diagram of a medical system for delivering OSA therapy. In system 10, implantable medical device (IMD) 16 and lead 20 are implanted in patient 14. IMD 16 includes housing 15 enclosing circuitry of IMD 16. In some examples, IMD 16 includes connector assembly 17, which is hermetically sealed to housing 15 and includes one or more connector bores for receiving a proximal end of at least one medical electrical lead 20 used for delivering OSA therapy. Although one lead 20 is illustrated in FIG. 1, there may be one or more leads 20 to which IMD 16 is coupled.

Lead 20 may include a flexible, elongate lead body 22, also called elongated member 22, that extends from lead proximal end 24 to lead distal end 26. As illustrated, lead 20 includes one or more electrodes 30 that are carried along a lead distal portion adjacent lead distal end 26 and are configured for insertion within the protrusor muscles 42A, 42B, and 46 of tongue 40. As one example, the genioglossus muscle includes oblique compartment 42A and horizontal compartment 42B. In this disclosure, the genioglossus muscle is referred to as protrusor muscle 42. Protrusor muscle 46 is an example of the geniohyoid muscle.

As illustrated, distal end 26 of lead 20 includes one or more electrodes 30. Proximal end 24 of lead 20 includes one or more electrical contacts to connect to connector assembly 17. Lead 20 also includes conductors such as coils or wires that connect respective electrodes 30 to respective electrical contacts at proximal end 24 of lead 20.

While protrusor muscles 42 and 46 are described, the example techniques described in this disclosure are not limited to stimulating protrusor muscles 42 and 46. Also, FIG. 1 illustrates one set of protrusor muscles 42 and 46 (e.g., on a first side of tongue 40). The other side of tongue 40 also includes protrusor muscles. For instance, a left side of tongue 40 includes a first set of protrusor muscles 42 and 46, and a right side of tongue 40 includes a second set of protrusor muscles.

In some examples, a surgeon may implant one or more leads 20 such that one or more electrodes 30 are implanted within soft tissue, such as musculature, proximate to medial branches of one or both hypoglossal nerves. In some examples, one or more electrodes 30 may be approximately 5 mm (e.g., 2 mm to 8 mm) from a major trunk of the hypoglossal nerve. In some examples, one or more electrodes 30 may be placed in an area of protrusor muscles 42 and 46 that include motor points, where each nerve axon terminates in the muscle (also called the neuro-muscular junction). The motor points are not at one location but spread out in the protrusor muscles. Leads 20 may be implanted such that one or more electrodes 30 may be generally in the area of the motor points (e.g., such that the motor points are within 1 to 10 mm from one or more electrodes 30). Examples of motor points for protrusor muscles 42 and 46 are illustrated in more detail with respect to FIG. 3.

Tongue 40 includes a distal end (e.g., tip of tongue 40), and electrodes 30 may be implanted proximate to root 49 of tongue 40. The surgeon may implant one or more leads 20 such that one or more electrodes are implanted proximate to root 49 of tongue 40, as illustrated in FIG. 1. For example, the location for stimulation for the genioglossus muscle 42 may be approximately 30 mm (e.g., 25 mm to 35 mm) from the Symphysis of the jaw (e.g., where the genioglossus and hypoglossal muscles insert). The location for stimulation for the geniohyoid muscle 46 may be approximately 40 mm (e.g., 35 mm to 45 mm) from the Symphysis. For both the genioglossus muscle 42 and the geniohyoid muscle 44, the location for stimulation may be approximately 11 mm (e.g., 7 mm to 15 mm) lateral to the midline on both the right and left sides of tongue 40 for stimulating respective hypoglossal nerves. In some examples, rather than stimulating hypoglossal nerves, the examples described in this disclosure may be configured for stimulating the motor points, as described in more detail with respect to FIG. 3. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 30 of lead 20 may be ring electrodes, segmented electrodes, partial ring electrodes, or any suitable electrode configuration. Ring electrodes extend 360 degrees around the circumference of the lead body of lead 20. Segmented and partial ring electrodes each extend along an arc less than 360 degrees (e.g., 90-120 degrees) around the outer circumference of the lead body of lead 20. In this manner, multiple segmented electrodes may be disposed around the perimeter of lead 20 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 20 may be, at least in part, paddle-shaped (e.g., a "paddle" lead), and may include an array of electrodes arranged as contacts or pads on a common surface, which may or may not be substantially flat and planar.

As described above, in some examples, electrodes 30 are within the musculature of tongue 40. Accordingly, one or more electrodes 30 may be "intramuscular electrodes." Intramuscular electrodes may be different than other electrodes that are placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 30 being "intramuscular electrodes," one or more electrodes 30 may be implanted in connective tissue or other soft tissue proximate to the hypoglossal nerve.

In some examples, lead 20 may be configured for advancement through the soft tissue, which may include the protrusor muscle tissue, to anchor electrodes 30 in proximity to the hypoglossal nerve(s) that innervate protrusor muscles 42 and/or 46 and/or motor points that connect axons of hypoglossal nerve(s) to respective muscle fibers of protrusor muscles 42 and/or 46. However, in some examples, lead 20 may be configured for advancement through vasculature of tongue 40. As one example, a surgeon may implant lead 20 in the lingual veins near the hypoglossal nerve through venous access in the subclavian vein. In such examples, one or more electrodes 30 may be "intravascular electrodes."

As described above, electrical stimulation therapy generated by IMD 16 and delivered via one or more electrodes 30 may activate protrusor muscles 42 and 46 to move tongue 40 forward, for instance, to promote a reduction in obstruction or narrowing of the upper airway 48 during sleep. As used herein, the term "activated" with regard to the electrical stimulation of protrusor muscles 42 and 46 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 42 and 46 and motor points and subsequent depolarization and mechanical contraction of the protrusor muscle cells of protrusor muscles 42 and 46. In some examples, protrusor muscles 42 and 46 may be activated directly by the electrical stimulation therapy.

Protrusor muscles 42 and/or 46, on a first side of tongue 40 (e.g., the left or right side of tongue 40), may be activated by a medial branch of a first hypoglossal nerve, and the protrusor muscles, on a second side of tongue 40 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 40, are activated by a lateral branch of the hypoglossal nerve.

One or more electrodes 30 may be used to deliver bilateral or unilateral stimulation to protrusor muscles 42 and 46 via the medial branch of the hypoglossal nerve or branches of the hypoglossal nerve (e.g., such as at the motor point where a terminal branch of the hypoglossal nerve interfaces with respective muscle fibers of protrusor muscles 42 and/or 46). For example, one or more electrodes 30 may be coupled to output circuitry of IMD 16 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 16 may deliver electrical stimulation to selectively activate protrusor muscles 42 and/or 46 or portions of protrusor muscles 42 and/or 46 during unilateral stimulation of the left or right protrusor muscles.

In some examples, one lead 20 may be implanted such that one or more of electrodes 30 deliver electrical stimulation to the left hypoglossal nerve or motor points of protrusor muscles on the left side of tongue, and therefore cause the left protrusor muscles to activate. In such examples, the electrical stimulation from one or more electrodes 30 may not be of sufficient amplitude to stimulate the right hypoglossal nerve or motor points of protrusor muscles on the right side of tongue and cause the right protrusor muscles to activate. In some examples, one lead 20 may be implanted such that one or more of electrodes 30 deliver electrical stimulation to stimulate the right hypoglossal nerve or motor points of protrusor muscles on the right side of tongue, and therefore cause the right protrusor muscles to activate. In such examples, the electrical stimulation from one or more electrodes 30 may not be of sufficient amplitude to stimulate the left hypoglossal nerve or motor points of protrusor muscles on the left side of tongue and cause the left protrusor muscles to activate. Accordingly, in some examples, two leads like lead 20 may be implanted to stimulate each of the left and right hypoglossal nerves and/or motor points of respective protrusor muscles on the left and right side of tongue 40.

In some examples, one lead 20 may be implanted substantially in the middle (e.g., center) of tongue 40. In such examples, one or more electrodes 30 may deliver electrical stimulation to both hypoglossal nerves or motor points of both muscles on the both sides of tongue 40, causing both hypoglossal nerves or motor points to activate respective left and right protrusor muscles. It may be possible to utilize current steering and field shaping techniques such that one or more electrodes 30 deliver first electrical stimulation that stimulates the left hypoglossal nerve or motor points of protrusor muscles on the left side of tongue 40 with little to no stimulation of the right hypoglossal nerve or motor points of protrusor muscles on the right side of tongue 40, and then one or more electrodes 30 deliver second electrical stimulation that stimulates the right hypoglossal nerve or motor points of protrusor muscles on the right side of tongue with little to no stimulation of the left hypoglossal nerve or motor points of protrusor muscles on the left side of tongue. In examples where two leads like lead 20 are utilized, each lead may alternate delivery of stimulation to respective hypoglossal nerves or motor points. In this way, IMD 16 may stimulate one hypoglossal nerve or one set of motor points and then the other hypoglossal nerve or another set of motor points, which can reduce muscle fatigue.

For instance, continuous stimulation may cause protrusor muscles to be continuously in a protruded state. This continuous contraction may cause protrusor muscles 42 and/or 46 to fatigue. In such cases, due to fatigue, the stimulation may not cause protrusor muscles 42 and/or 46 to maintain a protruded state (or higher intensity of the electrical stimulation may be needed to cause protrusor muscles 42 and/or 46 to remain in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 40, while permitting the protrusor muscles 42 and/or 46 that were previously activated to rest. Hence, by cycling between alternate stimulation of the left and right protrusor muscles, tongue 40 can remain in the protruded state, while one of the first or second set of protrusor muscles is at rest.

In some examples, one lead 20 may be implanted laterally or diagonally across tongue 40 such that some of electrodes 30 on lead 20 can be used to stimulate the left hypoglossal nerve and/or motor points of the protrusor muscles on the left side of tongue 40 and some of electrodes 30 on the same lead 20 can be used to stimulate the right hypoglossal nerve and/or motor points of the protrusor muscles on the right side of tongue 40. In such examples, IMD 16 may selectively deliver electrical stimulation to a first hypoglossal nerve and/or first motor points of the protrusor muscles on the a first side of tongue 40 via a first set of one or more electrodes 30, and then deliver electrical stimulation to a second hypoglossal nerve and/or/or second set of motor points of the protrusor muscles on a second side of tongue 40 via a second set of one or more electrodes 30. This may be another way in which to reduce muscle fatigue.

Lead proximal end 24 includes a connector (not shown in FIG. 1) that may be coupled to connector assembly 17 of IMD 16 to provide electrical connection between circuitry enclosed by the housing 15 of IMD 16. Lead body 22 encloses electrical conductors extending from each of one or more electrodes 30 to the proximal connector at proximal end 24 to provide electrical connection between output circuitry of IMD 16 and the electrodes 30.

There may be various ways in which lead 20 is implanted in patient 14. As one example, a surgeon may insert a needle (also called introducer needle) through the lower part of the jaw and in tongue 40 starting from the back of tongue 40. The surgeon may insert the needle until a distal tip of the needle reaches a point at or adjacent to the tip of tongue 40, angling the needle to be extend proximate to the hypoglossal nerve (e.g., left or right hypoglossal nerve). In some examples, the needle may include one or more electrically conductive areas (e.g., one or more electrodes) at the distal end, and the surgeon may cause the one or more electrically conductive areas of the needle to output electrical stimulation (e.g., in the form of controlled current pulses or controlled voltage pulses), which in turn causes a physiological response such as activation of protrusor muscles 42 and/or 46 and protrusion of tongue 40. The surgeon may adjust the location of the needle based on the physiological response to determine a location in tongue 40 that provides effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 40. Then, the surgeon may remove the needle leaving behind the guidewire.

The surgeon may place an introducer sheath, which may or may not include a dilator, over the guidewire through the opening created by the introducer needle. In some examples, the introducer sheath may optionally include one or more electrodes that the surgeon can use to test stimulation of tongue 40 to ensure that lead 20 will be located in the correct location, relative to the target nerve tissue. Once the introducer sheath is in place, the surgeon may remove the guidewire. In some examples, the introducer sheath may be flexible or curved to ease placement of the introducer sheath in patient 14. The guidewire and the introducer sheath may help placement of lead 20 adjacent to or around the hypoglossal nerve. For example, using the guidewire and the introducer sheath may enable a lead having a diameter equal to or larger than the diameter of the introducer needle to the inserted in the opening created by the introducer needle.

In some examples, rather than or in addition to the introducer sheath having one or more electrodes, the introducer sheath may include one or more perforations. The one or more perforations may align with electrodes 30. Prior to placement of lead 20, the surgeon may place lead 20 into the introducer sheath such that electrodes 30 align with the perforations of the introducer sheath. A medical device may output stimulation signals through electrodes 30 and the perforations of the introducer sheath to stimulate the hypoglossal nerve and/or one or more motor points of the protrusor muscle within tongue 40. In this way, if further refinement is needed to determine the lead placement for lead 20, the surgeon may adjust the location of lead 20 in response to one or more electrical signal detected by electrodes 30 and through the perforation of the introducer sheath.

In some examples, the surgeon may directly insert lead 20 through the introducer needle without using the introducer sheath and the guidewire. In such examples, the introducer needle may be appropriately sized to receive lead 20 and may perform operations similar to those of the introducer sheath described above.

The surgeon may prepare lead 20 for insertion. In some examples, there may be an additional sheath placed over lead 20 that holds fixation member(s), such as those described with respect to FIG. 2, in place. Use of such an additional sheath is not necessary in all examples. For instance, the introducer sheath may be configured to hold the fixation member(s) in place. Because lead 20 may be highly flexible, in some examples, the surgeon may place a stylet through lead 20 to provide some rigidity and allow lead 20 to traverse through tongue 40 under a pushing force. Use of a stylet may not be necessary in all examples.

The surgeon may put lead 20 through the introducer such that one or more electrodes 30 are proximate to the hypoglossal nerve (e.g., such that distal end 26 is near tip of tongue as one non-limiting example). Electrodes 30 may be proximate to the hypoglossal nerve and/or motor points of the protrusor muscles due to the needle creating an opening near the hypoglossal nerve and/or motor points of the protrusor muscle. The surgeon may then tunnel proximal end 24 of lead 20 back to a connection with IMD 16.

In this manner, the surgeon may implant one lead 20. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 20, the introducer needle, and/or the introducer sheath.

FIG. 1 illustrates the location of IMD 16 as being within or proximate to the neck of patient 14. However, IMD 16 may be implanted in various other locations. As one example, the surgeon may implant IMD 16 in the left or right pectoral region. For instance, the surgeon may plan on implanting IMD 16 in the left pectoral region unless another medical device is already implanted in the left pectoral region. If another medical device is already implanted in the left pectoral region, the surgeon may then implant IMD 16 in the right pectoral region. There may include other locations where the surgeon may implant IMD 16, such as the back of patient 14. The example techniques are not limited to any particular implant location of IMD 16.

In accordance with one or more examples described in this disclosure, system 10 is an implant system for utilizing lead 20 in tongue 40 for treatment of OSA. In some example, the system may be configured such that substantial dissection is not required to expose one or more hypoglossal nerves and/or one or more motor points of the protrusor muscle within tongue 40 for placement of the lead. This disclosure describes examples of system 10 configured for placement of lead 20 in a way that minimizes access incisions for placement of lead 20.

In some situations, it may be desirable to include multiple electrodes on lead 20 to achieve desired physiological effects (e.g., therapeutic effects). For example, to achieve the desired effect, multiple electrodes may be used to target different fibers of the same nerve (e.g., target one or more motor points of the protrusor muscle within tongue 40). In such cases, determining the locations of the different fibers or motor points one at a time is time-consuming and may cause nerve injury. In some examples, system 10 may enable a surgeon to identify the locations of different fibers or motor points of the protrusor muscles in such a manner to shorten the surgical time and reduce the risk of nerve injury.

As described above, system 10 is an implant system for implanting lead 20 adjacent to or around one or more hypoglossal nerves and/or motor points without open surgery, so that lead 20 may be implanted to stimulate the nerves with minimal impact to patient 14. There may be certain unique challenges associated with implanting lead 20 adjacent to or around the hypoglossal nerves and/or the one or more motor points of the protrusor muscle in tongue 40 without open surgery. As one example, without performing an open surgery to expose the hypoglossal nerves and/or motor points, there are difficulties with localizing and accessing the hypoglossal nerves and/or motor points.

To identify the location of a hypoglossal nerve and/or a motor point without performing an open surgery, system 10 may include an introducer needle for creating an opening in the tongue of the patient for implantation of lead 20 and a medical device for delivering stimulation signals through the introducer needle to the tongue of the patient to stimulate the hypoglossal nerve and/or the motor point. The same medical device or possibly another medical device may further receive electrical signals from lead 20, where the electrical signals (e.g., EMG signals) are generated from a muscle movement in response to the stimulation signals. As illustrated in FIG. 1, the medical device may be an implantable medical device (e.g., IMD 16) implanted near the neck of patient 14. Hence, IMD 16 may be utilized for chronic (i.e., long-term) treatment of OSA. However, in some examples, during the implantation of lead 20 or determining location for implanting lead 20, a trial stimulator (e.g., external medical device) may be used to deliver stimulation to the introducer needle or through lead 20 when lead 20 is within the introducer sheath. Accordingly, the medical device may be an external medical device coupled to the introducer needle for delivering stimulation signals. In some examples, a first medical device may be utilized to stimulate the electrically conducive areas on the introducer needle, and a second different medical device may be utilized to stimulate electrodes 30 when lead 20 is within the introducer sheath. In some examples, the first medical device and the second medical device may be the same medical device. It should be noted that IMD 16 may also be used as a trial stimulator, and the techniques are not limited to an external medical device.

As described below in further detail, the introducer needle may be inserted through tongue 40 to a proximate position of the hypoglossal nerve and/or the motor point in tongue 40. The introducer needle may include an elongated body having one or more electrically conductive areas for delivering OSA therapies. The introducer needle may couple with a medical device to deliver one or more stimulation signals from the medical device to the tongue of the patient. The one or more electrically conductive areas (e.g., two electrically conductive areas, three electrically conductive areas, or four electrically conductive areas, etc.) of the elongated body may deliver the one or more stimulation signals to tongue 40 to stimulate the hypoglossal nerve and/or the motor point to innervate one or more of a genioglossal or geniohyoid muscle. The one or more electrically conductive areas of the introducer needle may also detect one or more electrical signals that are generated based on the movements of the genioglossal and/or geniohyoid muscle.

For example, after insertion of the introducer needle, the introducer needle may be coupled with a medical device to deliver a stimulation signal through the one or more electrically conductive areas of the introducer needle to stimulate a hypoglossal nerve and/or one or more motor points of the protrusor muscle within tongue 40. In response to the stimulation signal, the hypoglossal nerve may innervate protrusor muscles 42 or 46 or the activation of the one or more motor points may cause protrusor muscles 42 or 46 to protrude, and one or more electrically conductive areas of the introducer needle may detect electrical signals (e.g., EMG signals) that represents the movement of protrusor muscles 42 or 46. In such examples, the medical device may receive the electrical signals detected by the one or more electrically conductive areas of the introducer needle and output information indicative of the electrical signals. In some examples, the medical device that outputs the stimulation signal may be different than the medical device that receives the electrical signals detected by the electrically conductive areas on the introducer needle, or the medical device that outputs the stimulation signal may be the same as the medical device that receives the electrical signals detected by the electrically conductive areas on the introducer needle. Based on the output information indicative of the electrical signals, a surgeon may determine a target treatment site for placement of lead 20.

Accordingly, system 10 is an example of an implant system for implanting lead 20 for treatments of OSA. System 10 includes an introducer needle that has an elongated body (e.g., the needle body).

The elongated body may be a malleable elongated body so that a surgeon can bend the desired shape for properly introducing lead 20. In some examples, the elongated body may be steerable so the surgeon can align lead 20 in a proper configuration intraoperatively. Having steerability in the elongated body may make it easier for surgeons to deploy lead 20 alongside and in proximity to a hypoglossal nerve and/or a motor point in tongue 40 of patient 14.

The elongated body includes one or more electrically conductive areas for delivering stimulation signals that can protrude tongue 40 for determining stimulation location for OSA therapies. The one or more electrically conductive areas of the introducer needle are located at a distal end of the elongated body. At the distal end of the introducer needle should not be interpreted to be limited mean that there is an electrically conductive area exactly at the distal end, although having an electrically conductive area exactly at the distal end is possible. Rather, "at the distal end" means that the one or more electrically conductive areas are proximate to the distal end of the introducer needle, including possibly being exactly at the distal end of the introducer needle. As one example, multiple electrically conductive areas may be longitudinally located relative to each other at the same axial position of the introducer needle. As another example, multiple electrically conductive areas may be circumferentially located relative to each other along an outer perimeter of the elongated body of the introducer needle in a direction orthogonal to the axial of the introducer needle.

System 10, along with the introducer needle, also includes a medical device for delivering stimulation signals via the introducer needle through the one or more electrically conductive areas to tongue 40 of patient 14 to stimulate a hypoglossal nerve and/or a motor point in tongue 40 of patient 14. The medical device may also receive one or more electrical signals detected by the introducer needle and output information indicative of the one or more electrical signals. For example, the medical device may receive an EMG signal that measures an electrical current generated from a muscle contraction in response to the stimulation signal.

For instance, a surgeon may insert the introducer needle in tongue 40 of patient 14 such that the one or more electrically conductive areas of the introducer needle are pushed through tissue near a chin of the patient and through the tongue proximate to the hypoglossal nerve and/or the motor point of a protrusor muscle within tongue 40. After inserting the introducer needle, the surgeon may control the medical device to deliver a stimulation signal via the introducer needle through the one or more electrically conductive areas to tongue 40 of patient 14 to stimulate the hypoglossal nerve and/or the motor point in tongue 40 of patient 14. The surgeon may also control the medical device (same or different medical device) to receive electrical signals detected by the introducer needle and output information indicative of the one or more electrical signals on a display device. The surgeon may then determine a target treatment site based on the output information indicative of the one or more electrical signals.

In some examples, system 10 may further include an introducer sheath having one or more perforations. The one or more perforations of the introducer sheath are aligned with the one or more electrically conductive areas of the introducer needle. The one or more perforations of the introducer sheath are further aligned with electrodes 30 of lead 20.

In some examples, lead 20 may have a relatively large diameter. For example, lead 20 may have a diameter equal to or larger than the diameter of the introducer needle so that lead 20 may not be inserted in the lumen of the elongated body of the introducer needle.

For instance, instead of insert lead 20 in the lumen of the elongated body of the introducer needle, the surgeon may insert a guidewire in the lumen of the elongated body, remove the introducer needle while leave the guidewire in tongue 40 of patient 14, and slide the introducer sheath over the guidewire so that the one or more perforations of the introducer sheath reach the hypoglossal nerve and/or the motor point in tongue 40 of patient 14.

After inserting the introducer sheath in and through the opening created by the introducer needle, the surgeon may remove the guidewire and insert lead 20 in the introducer sheath so that electrodes 30 of lead 20 are aligned with the one or more perforations of the introducer sheath. The surgeon may also control a medical device to output stimulation signals through electrodes 30 and the perforations of the introducer sheath to stimulate the hypoglossal nerve and/or the motor point. In this way, a lead having a diameter equal to or larger than the diameter of the introducer needle may be inserted in and through the opening created by the introducer needle.

Figure 2:
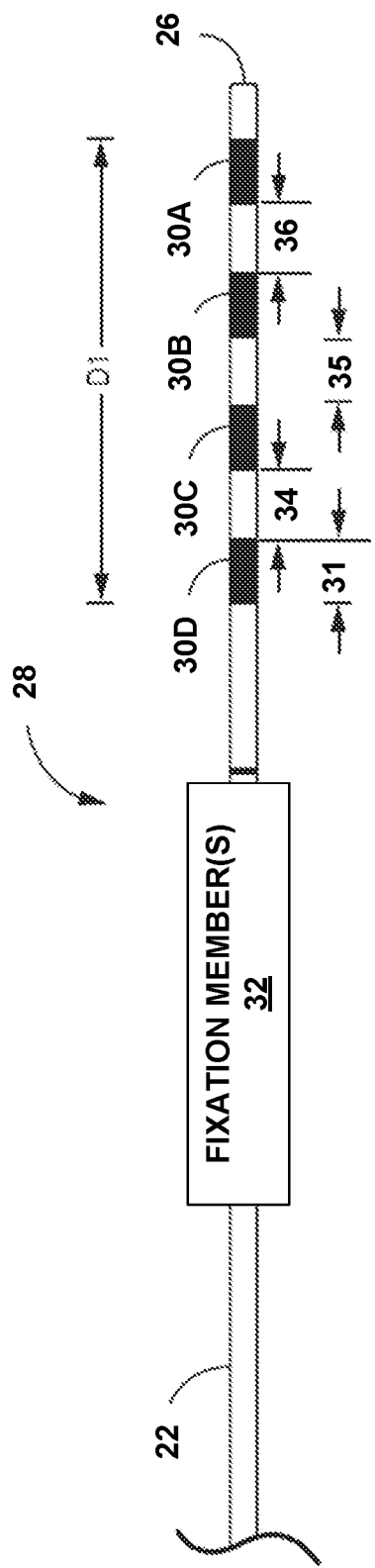
FIG. 2 is a conceptual diagram of a lead used for OSA therapy according to one or more examples of this disclosure.

FIG. 2 is a conceptual diagram of lead 20 used for OSA therapy according to one or more examples. For instance, FIG. 2 illustrates distal portion 28 of lead 20, where distal portion 28 of lead 20 may form part of lead 20 that is implanted in tongue 40, as described above. Lead 20 may include one or more electrodes 30, and FIG. 2 shows lead 20 with four electrodes 30A, 30B, 30C, and 30D (collectively referred to as "electrodes 30") spaced apart longitudinally along lead body 22. Lead body 22 is an example of the elongated member of lead 20. For instance, lead body 22 and the elongated member of lead 20 are the same.

Lead body 22 (e.g., elongated member of lead 20) may be a flexible lead body through which insulated electrical conductors extend to respective electrodes 30. The distal most electrode 30A may be adjacent or proximate to lead distal end 26. Each of electrodes 30 may be spaced proximally from the respective adjacent one of electrodes 30 by respective interelectrode distances 34, 35 and 36.

The electrical conductors that extend to respective electrodes 30 from proximal contacts at proximal end 24 may be arranged as a plurality of coils. The coils may increase the flexibility of lead 20 so that lead 20 can bend at the distal end. In some examples, the coils may be exposed along the locations of electrodes 30 such that the coils form electrodes 30. Rather than electrodes 30 being pad electrodes or ring electrodes, the coils form electrodes 30 and, in this way, electrodes 30 are bendable, providing additional flexibility. In such examples, electrodes 30 are coil electrodes.

In some examples, each one of electrodes 30 may have equivalent electrode lengths 31 (e.g., longitudinal extend of electrodes 30 along lead body 22). Lengths 31 may be approximately 3 mm, but less than 3 mm lengths are possible. However, electrodes 30 may have electrode lengths 31 that are different from each other in order (e.g., to optimize placement of the electrodes 30 or the resulting electrical field of stimulation relative to targeted stimulation sites corresponding to left and right hypoglossal nerves or branches of hypoglossal nerves and/or motor points of protrusor muscles 42 and/or 46).

Spacing 34, 35, and 36 are shown to be approximately equal in FIG. 2. However, in other examples, the interelectrode spacings 34, 35, and 36 may be different from each other (e.g., in order to optimize placement of electrodes 30 relative to the targeted stimulation sites). Spacing 34, 35, and 36 may be approximately 3 mm but less than 3 mm spacing is possible. In some examples, for a bipolar configuration, electrodes 30A and 30B form an anode and cathode pair for delivering bipolar stimulation in one portion of the protrusor muscles 42 and/or 46 (e.g., either the left or right protrusor muscles or a proximal and/or distal portion of portion of the protrusor muscles). Electrodes 30C and 30D may form a second anode and cathode pair for delivering bipolar stimulation in a different portion of protrusor muscles 42 and/or 46 (e.g., the other of the left or right portions or the other of the proximal or distal portions). Accordingly, the interelectrode spacing 35 between the two bipolar pairs 30A, 30B and 30C, 30D may be different than the interelectrode spacing 34 and 36 between the anode and cathode within each bipolar pair 30A, 30B and 30C, 30D.

In some examples, for a unipolar configuration, housing 15 of IMD 16 may include an electrode that functions as cathode, and part of the anode and cathode pair with one of electrodes 30. In some examples, housing 15 itself may function as the cathode of an anode, cathode pair, with one of electrodes 30 forming the anode. Housing 15 may be anode in some examples.

In one example, the total distance D1 encompassed by electrodes 30 along the distal portion 28 of lead body 22 may be between approximately 20 and 30 millimeters. In one example, the total distance D1 is between approximately 20 and 22 millimeters. However, as an alternative, the distances may be shorter. As one example, the distance from distal portion 28 to one or more fixation members 32 may be approximately 10 millimeters to ensure that at least one of the one or more fixation members 32 is implanted within tongue 40.

The interelectrode spacings 34 and 36 within a proximal electrode pair 30C, 30D and a distal electrode pair 30A, 30B, respectively, may be in a range of approximately 2 to 5 millimeters in some examples. The interelectrode spacing 35 separating the distal and proximal pairs 30A, 30B and 30C, 30D may be greater than the interelectrode spacings 34 and 36. For example, the interelectrode spacing 35 may be in a range of approximately 4 to 6 millimeters in some examples. In one example, each of electrodes 30 has an electrode length 31 of approximately 3 mm, and each of interelectrode spacings 34, 35 and 36 is approximately 3 mm.

In FIG. 2, each of electrodes 30 is a circumferential ring electrode which may be uniform in diameter with lead body 22. As described above, electrodes 30 may include other types of electrodes such as a tip electrode, a helical electrode, a coil electrode, as described above, segmented electrodes, a button electrode as examples. For instance, the distal most electrode 30A may be provided as a tip electrode at the lead distal end 26 with the remaining three electrodes 30B, 30C, and 30D being ring electrodes. In some examples, when electrode 30A is positioned at the distal end 26, electrode 30A may be a helical electrode configured to screw into the muscle tissue at the implant site to additionally serve as a fixation member for anchoring the distal portion 28 of lead 20 at the targeted therapy delivery site. In some examples, one or more of electrodes 30 may be a hook electrode or barbed electrode to provide active fixation of the distal portion 28 of lead 20 at the therapy delivery site.

Lead 20 may include one or more fixation members 32 for minimizing the likelihood of lead migration. Fixation member 32 may include multiple sets of tines which engage the surrounding tissue when lead distal portion 28 is positioned at the target therapy delivery site. The tines of fixation member 32 may extend radially outward and proximally at an angle relative to the longitudinal axis of lead body 22 to prevent or reduce retraction of lead body 22. For instance, the tines may include springs that in an uncompressed state extend the tines outwards. Tines of fixation member 32 may be collapsible against lead body 22 when lead 20 is held within the confines of a lead delivery tool (e.g., an introducer needle or an introducer sheath) used to deploy lead distal portion 28 at the target implant site. Upon removal of the lead delivery tool, the tines of fixation member 32 may spread to a normally extended position (e.g., due to the spring bias) to engage with surrounding tissue and resist proximal and lateral migration of lead body 22. For instance, the tines may be normally biased to the extended position but retracted against the introducer sheath for implantation. When the introducer sheath is removed, the tines extend outward to their uncompressed state. Examples of the tines for fixation members 32 include tines 31 of FIG. 1. In some examples, fixation member 32 may additionally or alternatively include one or more hooks, barbs, helices, or other fixation mechanisms extending from one or more longitudinal locations along lead body 22 and/or lead distal end 26.

In some examples, the tines, when deployed, may be forward facing and/or backward facing. Forward facing means that the portion of the tines that are more proximate to proximal end 24 spread out when deployed. For instance, the tine has a connection point on lead body 22 and a free arm of the tine that extends away from the lead body 22, and the portion of the free arm that is more proximate to proximal end 24 extends. Backward facing means that the portion of the tines that are more proximate to distal end 26 spread out when deployed. For instance, the tine has a connection point on lead body 22 and a free arm of the tine that extends away from the lead body 22, and the portion of the free arm that is more proximate to distal end 26 extends. Having both forward and backward facing tines may reduce lateral and proximal migration.

Fixation members 32 may partially or wholly engage one or more of protrusor muscles 42 and/or 46 and/or other muscles below tongue 40, and/or other soft tissues of the neck (e.g., fat and connective tissue), when proximal end of lead body 20 is tunneled to an implant pocket of IMD 16. In some examples, fixation member 32 may include one or more fixation mechanisms located at other locations, including at or proximate to distal end 26, between electrodes 30, or otherwise more distally or more proximally than the location shown in FIG. 2.

The implant pocket of IMD 16 may be in a pectoral region of patient 14. Lead body 22 may include proximal connectors that engage with connector assembly 17 of IMD 16. Accordingly, the length of the elongated lead body 22 from distal portion 28 to the lead proximal end 24 may be selected to extend from a target therapy delivery site in protrusor muscles 42 and/or 46 to a location in the pectoral region where IMD 16 is implanted. The length of lead body 22 (e.g., elongated member) may be up to 10 cm or up to 20 cm as examples but may generally be 25 cm or less, though longer or shorter lead body lengths may be used depending on the anatomy and size of patient 14.

Figure 3:
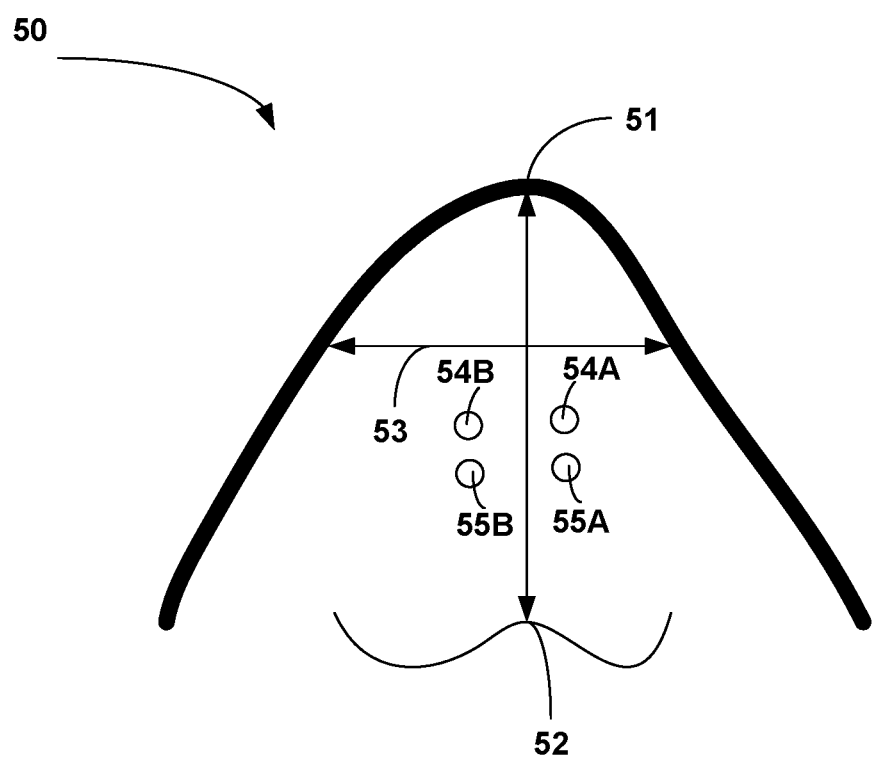
FIG. 3 is a conceptual diagram illustrating example locations of motor points where stimulation for OSA therapy may be delivered.

FIG. 3 is a conceptual diagram illustrating example locations of motor points where stimulation for OSA therapy may be delivered. FIG. 3 illustrates jaw 50 of patient 14, where patient 14 is in a supine position and jaw 50 of patient 14 is viewed from an inferior location of patient 14. For instance, FIG. 3 illustrates symphysis 51 and hyoid bone 52. In the example illustrated in FIG. 3, the line interconnecting symphysis 51 and hyoid bone 52 may be considered as a y-axis along the midline of tongue 40. FIG. 3 also illustrates intergonial distance 53 between the two gonia of patient 14, where the gonia is a point on each side of the lower jaw 50 at the mandibular angle. Intergonial distance 53 may be along the x-axis of tongue 40.

FIG. 3 illustrates motor points 54A and 54B and motor points 55A and 55B. Motor points 54A may be motor points for the right genioglossus muscle, and motor points 54B may be motor points for the left genioglossus muscle. Motor points 55A may be motor points for the right geniohyoid muscle, and motor points 55B may be motor points for the left geniohyoid muscle. Motor points 54A and 54B and motor points 55A and 55B may genericize the motor points for each muscle for purposes of illustration. There may be additional motor points and/or motor points at different locations for each muscle.

In one or more examples, lead 20 and/or one or more electrodes 30 may be implanted proximate to motor points 54A, 54B, 55A, or 55B for stimulating at motor points 54A, 54B, 55A, and/or 55B. For instance, in examples where two leads are implanted, a first lead and its electrodes may be implanted proximate to motor points 54A and/or 55A and a second lead and its electrodes may be implanted proximate to motor points 54B and/or 55B. In one or more examples, electrodes 30 may be approximately 1 mm to 10 mm from respective motor points 54A, 54B, 55A, or 55B.

A hypoglossal nerve (e.g., on the left or right side of tongue 40) initially is a trunk of nerves fibers called axons. The axons of the hypoglossal nerve branch out. For example, the trunk of hypoglossal nerve includes multiple sets of axons including a first set of axons, and the first set of axons branch out from the trunk of the hypoglossal nerve. The first set of axons include multiple groups of axons including a first group of axons, and the first group of axons branch out from the first set of axons, and so forth. The locations where the branched-out axons interface with respective muscle fibers of protrusor muscles 42 and/or 46 (e.g., genioglossus and/or geniohyoid muscle) are referred to as motor points.

For instance, a branch of the hypoglossal nerve that interfaces (e.g., connects at the neuro-muscular junction) with the muscle fiber is referred to as a terminal branch, and the end of the terminal branch is a motor point. The length of a terminal branch may be approximately 10 mm from the hypoglossal nerve to the genioglossal or geniohyoid muscles. In some examples, there may be approximately an average of 1.5 terminal branches with a standard deviation of ±0.7 for the right geniohyoid muscle, an average of 4.8 terminal branches with a standard deviation of ±1.4 for the right genioglossus muscle, an average of 2.0 terminal branches with a standard deviation of ±0.9 for the left geniohyoid muscle, and an average of 5.1 terminal branches with a standard deviation of ±1.9 for the left genioglossus muscle.

There may be possible advantages with stimulating at motor points 54A, 54B, 55A, or 55B, as compared to some other techniques. For instance, some techniques utilize cuff electrodes or stimulate at the hypoglossal nerve. Due to the different bifurcation patterns, placing a cuff electrode around the hypoglossal nerve, or generally attaching an electrode to the hypoglossal nerve can be challenging. Also, where cuff electrodes or electrodes that attach to the hypoglossal nerve are used, implanting electrodes around or at each of the hypoglossal nerves requires multiple surgical entry points to attached to both hypoglossal nerves. Moreover, utilizing cuff electrodes or electrodes that attach to the hypoglossal nerves can possibly negatively impact the nerve by tugging, stretching, or otherwise causing irritation. Accordingly, utilizing lead 20 and electrodes 30 that are implanted proximate to the motor points may be beneficial (e.g., less surgery to implant and less impact on the nerve) as compared to techniques where cuff electrodes or electrodes implanted on the hypoglossal nerve are utilized.

Furthermore, stimulating at motor points 54A, 54B, 55A, and/or 55B, such as at the bifurcation point of a motor neuron that attach to muscle fibers, may provide advantages such as for better control of muscle movement. Because motor points 54A, 54B, 55A, and 55B are spatially distributed, by stimulating motor points 54A, 54B, 55A, and/or 55B, the amount of the genioglossus and geniohyoid muscle that is being stimulated can be controlled. Also, stimulating at motor points 54A, 54B, 55A, and/or 55B may allow for more gentle muscle activation. For instance, when stimulation is provided near the trunk of the hypoglossal nerve, even stimulation signal with relatively small amplitude can cause the genioglossus and/or geniohyoid muscle to fully protrude (e.g., there is high loop gain where small stimulation amplitudes cause large muscle protrusion). Fine tuning of how much to protrude the genioglossus and/or geniohyoid muscle may not be available when stimulating at a trunk of the hypoglossal nerve. However, there may be lower loop gain stimulating at motor points 54A, 54B, 55A, and/or 55B. For instance, a stimulation signal having a lower amplitude may move cause the genioglossus and/or geniohyoid muscle to protrude a small amount, and a stimulation signal having a higher amplitude may move cause the genioglossus and/or geniohyoid muscle to protrude a higher amount when stimulating at motor points 54A, 54B, 55A and/or 55B.

The following are example locations of motor points 54A, 54B, 55A, and 55B relative to the midline (x-axis), posterior symphysis 51 (y-axis), and depth (z-axis), where the depth is from the plane formed by the inferior border of symphysis 51 and anterior border of hyoid bone 52.

Motor points 54A may be for the right genioglossus muscle and may be located at 13.48 mm±3.59 from the x-axis, 31.01 mm±6.96 from the y-axis, and 22.58 mm±3.74 from the z-axis. Motor points 55A may be for the right geniohyoid muscle and may be located at 11.74 mm±3.05 from the x-axis, 41.81 mm±6.44 from the y-axis, and 16.29 mm+3.40 from the z-axis. Motor points 54B may be for the left genioglossus muscle and may be located at 9.96 mm±2.24 from the x-axis, 29.62 mm±9.25 from the y-axis, and 21.11 mm±4.10 from the z-axis. Motor points 55B may be for the left geniohyoid muscle and may be located at 11.45 mm±1.65 from the x-axis, 39.63 mm±8.03 from the y-axis, and 15.09 mm±2.41 from the z-axis.

Figure 4:
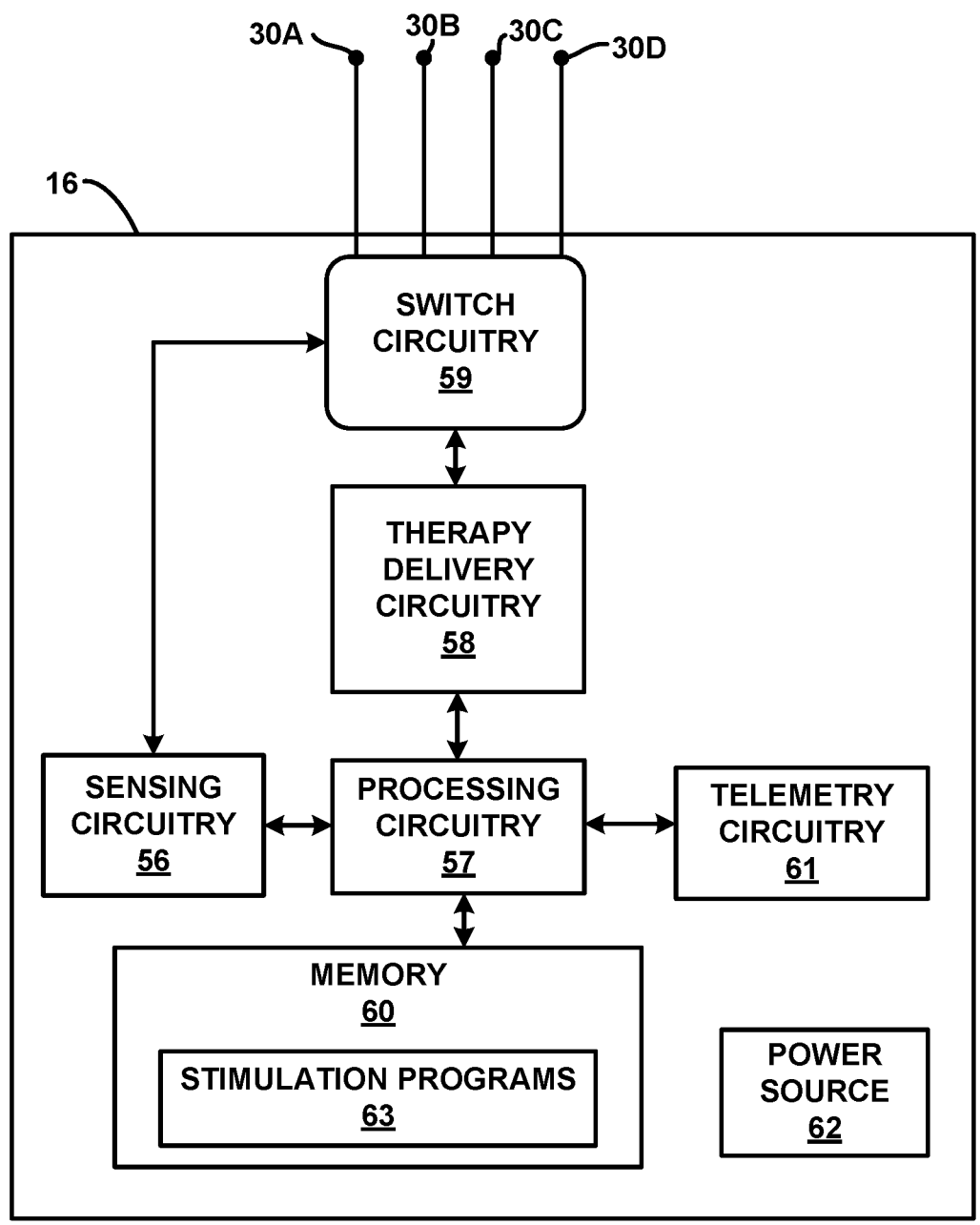
FIG. 4 is a block diagram illustrating example configurations of implantable medical devices (IMDs) which may be utilized in the system of FIG. 1.

FIG. 4 is block diagram illustrating example configurations of implantable medical devices (IMDs) which may be utilized in the system of FIG. 1. As shown in FIG. 4, IMD 16 includes sensing circuitry 56, processing circuitry 57, therapy delivery circuitry 58, switch circuitry 59, memory 60, telemetry circuitry 61, and power source 62. IMD 16 may include a greater or fewer number of components. For example, in some examples, such as examples in which IMD 16 deliver the electrical stimulation in an open-loop manner, IMD 16 may not include sensing circuitry 56.

Switch circuitry 59 may be configured to, in response to instructions from processing circuitry 57, switch the coupling of electrodes 30 between sensing circuitry 56 and therapy delivery circuitry 58. In examples where sensing circuitry 56 is not used, switch circuitry 59 may not be needed. However, even in examples where sensing circuitry 56 is not used, IMD 16 may include switch circuitry 59 such as to disconnect electrodes 30 from therapy delivery circuitry 58.

In some examples, therapy delivery circuitry 58 may include a plurality of regulated current sources or sinks, with each current source or sink coupled to one of electrodes 30. In such examples, therapy delivery circuitry 58 may control each current source or sink and switching between electrodes 30 may not be necessary for therapy delivery since each one of electrodes 30 is individually controllable.

Although not shown in FIG. 3, in some examples, IMD 16 may include one or more sensors configured to sense posture or position of patient 14. For example, IMD 16 may include accelerometer to determine if patient 14 is lying down. Another example of the one or more sensors is a motion sensor, and movement sensed by the motion sensor may indicate if patient 14 is having restless sleep, which may be indicative of the onset of OSA. Additional examples of the sensors include acoustical sensors or a microphone for detecting vibrations in upper airway 48. Vibrations in upper airway 48 may be indicative of the onset of OSA. In some examples, processing circuitry 57 may control delivery of therapy based on information received from the one or more sensors, such as delivery of therapy after sensing an onset of OSA.

In some examples, electrodes 30 may be configured to sense electromyogram (EMG) signals. Sensing circuitry 56 may be switchably coupled to electrodes 30 via switch circuitry 59 to be used as EMG sensing electrodes with electrodes 30 are not being used for stimulation. EMG signals may be used by processing circuitry 57 to detect sleep state and/or low tonal state of protrusor muscles 42 and/or 46 for use in delivering electrical stimulation. In some examples, rather than using electrodes 30 or in addition to using electrodes 30, there may be other electrodes or sensors used to sense EMG signals.

In general, IMD 16 may comprise any suitable arrangement of hardware, alone or in combination with software and/or firmware, to perform the techniques attributed to IMD 16 and processing circuitry 57, therapy delivery circuitry 58, and telemetry circuitry 61 of IMD 16. In various examples, IMD 16 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components.

The various units of IMD 16 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, one or more of the units may be distinct circuit blocks (fixed-function or programmable), and in some examples, one or more of the units may be integrated circuits.

IMD 16 may include arithmetic logic units (ALUs), elementary function units (EFUs), digital circuits, analog circuits, and/or programmable cores, formed from programmable circuits. In examples where the operations of IMD 16 are performed using software executed by the programmable circuits, memory 60 may store the instructions (e.g., object code) of the software that processing circuitry 57 receives and executes, or another memory within IMD 16 (not shown) may store such instructions.

IMD 16 also, in various examples, may include a memory 60, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although sensing circuitry 56, processing circuitry 57, therapy delivery circuitry 58, switch circuitry 59, and telemetry circuitry 61 are described as separate circuitry, in some examples, sensing circuitry 56, processing circuitry 57, therapy delivery circuitry 58, switch circuitry 59, and telemetry circuitry 61 are functionally integrated. In some examples, sensing circuitry 56, processing circuitry 57, therapy delivery circuitry 58, switch circuitry 59, and telemetry circuitry 61 correspond to individual hardware units, such as ASICs, DSPs, FPGAs, or other hardware units.

Memory 60 stores stimulation programs 63 (also called therapy programs 63) that specify stimulation parameter values for the electrical stimulation provided by IMD 16. Memory 60 may also store instructions for execution by processing circuitry 57, in addition to stimulation programs 63. Information related to sensed parameters of patient 14 (e.g., from sensing circuitry 56 or the one or more sensors of IMD 16) may be recorded for long-term storage and retrieval by a user, and/or used by processing circuitry 57 for adjustment of stimulation parameters (e.g., amplitude, pulse width, and pulse rate). In some examples, memory 60 includes separate memories for storing instructions, electrical signal information, and stimulation programs 63. In some examples, processing circuitry 57 may select new stimulation parameters for a stimulation program 63 or new stimulation program from stimulation programs 63 to use in the delivery of the electrical stimulation based on patient input and/or monitored physiological states after termination of the electrical stimulation.

Generally, therapy delivery circuitry 58 generates and delivers electrical stimulation under the control of processing circuitry 57. In some examples, processing circuitry 57 controls therapy delivery circuitry 58 by accessing memory 60 to selectively access and load at least one of stimulation programs 63 to therapy delivery circuitry 58. For example, in operation, processing circuitry 57 may access memory 60 to load one of stimulation programs 63 to therapy delivery circuitry 58.

By way of example, processing circuitry 57 may access memory 60 to load one of stimulation programs 63 to control therapy delivery circuitry 58 for delivering the electrical stimulation to patient 14. A clinician or patient 14 may select a particular one of stimulation programs 63 from a list using a programming device, such as a patient programmer or a clinician programmer. Processing circuitry 57 may receive the selection via telemetry circuitry 61. Therapy delivery circuitry 58 delivers the electrical stimulation to patient 14 according to the selected program for an extended period of time, such as minutes or hours while patient 14 is asleep (e.g., as determined from the one or more sensors and/or sensing circuitry 56). For example, processing circuitry 57 may control switch circuitry 59 to couple electrodes 30 to therapy delivery circuitry 58.

Therapy delivery circuitry 58 delivers electrical stimulation according to stimulation parameters. In some examples, therapy delivery circuitry 58 delivers electrical stimulation in the form of electrical pulses. In such examples, relevant stimulation parameters may include a voltage or current pulse amplitude, a pulse rate, a pulse width, a duty cycle, and/or the combination of electrodes 30 that therapy delivery circuitry 58 uses to deliver the stimulation signal. In some examples, therapy delivery circuitry 58 delivers electrical stimulation in the form of continuous waveforms. In such examples, relevant stimulation parameters may include a voltage or current amplitude, a frequency, a shape of the stimulation signal, a duty cycle of the stimulation signal, or the combination of electrodes 30 therapy delivery circuitry 58 uses to deliver the stimulation signal.

In some examples, the stimulation parameters for the stimulation programs 63 may be selected to cause protrusor muscles 42 and/or 46 to a protruded state (e.g., to open-up airway 48). An example range of stimulation parameters for the electrical stimulation that are likely to be effective in treating OSA (e.g., upon application to the hypoglossal nerves to cause protrusor muscles 42, 46 to protrude or upon application to motor points such as motor points 54A, 54B, 55A, and 55B), are as follows:

a. Frequency or pulse rate: between about 30 Hz and about 50 Hz. In some examples, the minimum target frequency is used which can achieve muscle tetany (e.g., constant contraction) and provide the required force to open the airway.

b. Current Amplitude: between about 0.5 milliamps (mA) and about 10 mA, and more generally from 0.5 mA to 3 mA, and approximately 1.5 mA.

c. Pulse Width: between about 100 microseconds (µs) and about 500 µs. In some examples, a pulse width of 150 µs might be used for reduced power consumption. In some particular examples, the pulse width is approximately 210 µs. In some cases, shorter pulse widths may be used in conjunction with higher current or voltage amplitudes.

Processing circuitry 57 may select stimulation programs 63 for alternating delivery of electrical stimulation between stimulating the left protrusor muscles 42 and/or 46 and the right protrusor muscles 42 and/or 46 on a time basis, such as in examples where two leads 20 are implanted. In some examples, there may be some overlap in the delivery of electrical stimulation such that for some of amount of time both left and right protrusor muscles 42 and/or 46 are being stimulated. In some examples, there may be a pause in alternating stimulation (e.g., stimulate left protrusor muscles, a time period with no stimulation, then stimulate right protrusor muscles, and so forth). Processing circuitry 57 may also select stimulation programs 63 that select between different combinations of electrodes 30 for stimulating, such as to stimulate different locations of the hypoglossal nerve(s), which may help with fatigue as well as provide more granular control of how much to protrude tongue 40.

In the example of FIG. 4, therapy delivery circuitry 58 drives electrodes 30 of lead 20. Specifically, therapy delivery circuitry 58 delivers electrical stimulation (e.g., regulated current or voltage pulses at pulse rates and pulse widths described above) to tissue of patient 14 via selected electrodes 30A-30D carried by lead 20. A proximal end of lead 20 extends from the housing of IMD 16 and a distal end of lead 20 extends to a target therapy site, such as one or both hypoglossal nerves and/or motor points 54A, 55A, 54B, and/or 55B. Therapy delivery circuitry 54 may deliver electrical stimulation with electrodes on more than one lead and each of the leads may carry one or more electrodes, such as when patient 14 is implanted with two leads 20 in tongue 40 for stimulating both hypoglossal nerves simultaneously or bilaterally (e.g., one after the other) or both motor points 54A and 54B and/or motor points 55A and 55B. The leads may be configured as an axial lead with ring electrodes or segmented electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 16.

In some examples, processing circuitry 57 may control therapy delivery circuitry 58 to deliver or terminate the electrical stimulation based on patient input received via telemetry circuitry 61. Telemetry circuitry 61 includes any suitable hardware, firmware, software or any combination thereof for communicating with another device, such as an external programmer. Under the control of processing circuitry 57, telemetry circuitry 61 may receive downlink telemetry (e.g., patient input) from and send uplink telemetry (e.g., an alert) to a programmer with the aid of an antenna, which may be internal and/or external. Processing circuitry 57 may provide the data to be uplinked to the programmer and the control signals for telemetry circuitry 61 and receive data from telemetry circuitry 61.

Generally, processing circuitry 57 controls telemetry circuitry 61 to exchange information with a medical device programmer and/or another device external to IMD 16. Processing circuitry 57 may transmit operational information and receive stimulation programs or stimulation parameter adjustments via telemetry circuitry 61. Also, in some examples, IMD 16 may communicate with other implanted devices, such as stimulators, control devices, or sensors, via telemetry circuitry 61.

Power source 62 delivers operating power to the components of IMD 16. Power source 62 may include a battery and a power generation circuit to produce the operating power. In some examples, the battery may be rechargeable to allow extended operation. Recharging may be accomplished through proximal inductive interaction between an external charger and an inductive charging coil within IMD 16. In other examples, an external inductive power supply may transcutaneously power IMD 16 whenever electrical stimulation is to occur.

Figure 5:
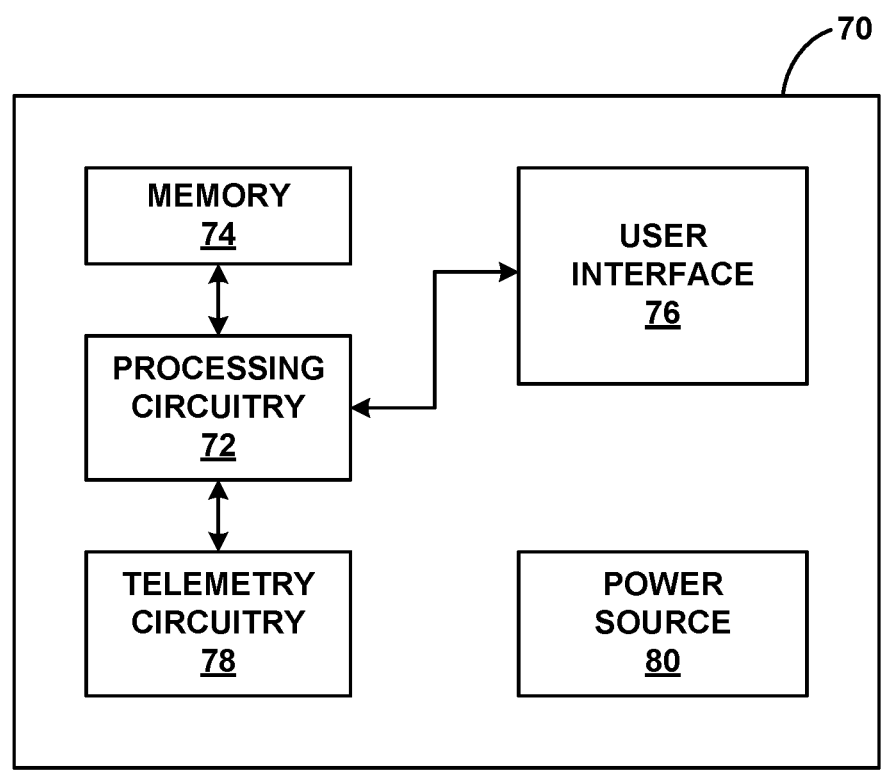
FIG. 5 is a block diagram illustrating an example configuration of an external programmer.

FIG. 5 is a block diagram illustrating an example configuration of an external programmer 70. While programmer 70 may generally be described as a hand-held computing device, the programmer may be a notebook computer, a cell phone, or a workstation, for example. As illustrated in FIG. 5, external programmer 70 may include processing circuitry 72, memory 74, user interface 76, telemetry circuitry 78, and power source 80.

In general, programmer 70 comprises any suitable arrangement of hardware, alone or in combination with software and/or firmware, to perform the techniques attributed to programmer 70, and processing circuitry 72, user interface 76, and telemetry module 78 of programmer 70. Examples of processing circuitry 72 may include one or more processors, such as one or more microprocessors, DSPs, ASICs, FPGAs, or any other equivalent integrated or discrete logic circuitry, as well as any combinations of such components. Examples of memory 74 include RAM, ROM, PROM, EPROM, EEPROM, flash memory, a hard disk, a CD-ROM, comprising executable instructions for causing the one or more processors to perform the actions attributed to them. Moreover, although processing circuitry 72 and telemetry circuitry 78 are described as separate circuitry, in some examples, processing circuitry 72 and telemetry circuitry 78 are functionally integrated. In some examples, processing circuitry 72 and telemetry circuitry 78 correspond to individual hardware units, such as ASICs, DSPs, FPGAs, or other hardware units.

In some examples, memory 74 may further include program information (e.g., stimulation programs) defining the electrical stimulation, similar to those stored in memory 60 of IMD 16. The stimulation programs stored in memory 74 may be downloaded into memory 60 of IMD 16.

User interface 76 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processing circuitry 72 may present and receive information relating to electrical stimulation and resulting therapeutic effects via user interface 76. For example, processing circuitry 72 may receive patient input via user interface 76. The input may be, for example, in the form of pressing a button on a keypad or selecting an icon from a touch screen.

Processing circuitry 72 may also present information to the patient in the form of alerts related to delivery of the electrical stimulation to patient 14 or a caregiver via user interface 76. Although not shown, programmer 70 may additionally or alternatively include a data or network interface to another computing device, to facilitate communication with the other device, and presentation of information relating to the electrical stimulation and therapeutic effects after termination of the electrical stimulation via the other device.

Telemetry circuitry 78 supports wireless communication between IMD 16 and programmer 70 under the control of processing circuitry 72. Telemetry circuitry 78 may also be configured to communicate with another computing device via wireless communication techniques, or direct communication through a wired connection. In some examples, telemetry circuitry 78 may be substantially similar to telemetry circuitry 61 of IMD 16 described above, providing wireless communication via an RF or proximal inductive medium. In some examples, telemetry circuitry 78 may include an antenna, which may take on a variety of forms, such as an internal or external antenna.

Examples of local wireless communication techniques that may be employed to facilitate communication between programmer 70 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 70 without needing to establish a secure wireless connection.

Power source 80 delivers operating power to the components of programmer 70. Power source 80 may include a battery and a power generation circuit to produce the operating power. In some examples, the battery may be rechargeable to allow extended operation.

FIG. 6A-6C are conceptual diagrams illustrating a lead and an example introducer needle which may be utilized in the system of FIG. 1. FIG. 6A illustrates an example of lead 90 that includes electrodes 98A and 98B at a distal end of the lead. FIG. 6B illustrates an example of introducer needle 110 formed from a conducting material, where the introducer needle includes an insulation coating that defines one or more electrically conductive areas. FIG. 6C illustrates the insertion of the lead 90 in the introducer needle 110. Lead 90 may be similar to lead 20 but may include fewer than the four electrodes 30, such as two electrodes 98A, 98B.

In the example illustrated in FIG. 6B, introducer needle 110 includes an elongated body 114 and an insulation coating 116. Introducer needle 110 is an example of the introducer needle described above for creating an opening in tongue 40 for lead placement of lead 20 or lead 90. The following is described with respect to lead 90, but the examples are applicable to lead 20 as well.

Elongated body 114 of introducer needle 110 is formed from any suitable conducting material, such as, but not limited to, stainless steel, cobalt-chrome alloy, titanium, nickel-titanium alloy (nitinol), gold, platinum, silver, iridium, tantalum, tungsten, or the like. Elongated body 114 includes a lumen 120, so that lead 90 may be inserted in lumen 120 of elongated body 114.

Insulation coating 116 includes openings 117A and 117B at a distal end 118 of elongated body 114, which defines electrically conductive areas 112A and 112B. Insulation coating 116 may be formed from any suitable non-conducting material, such as vinyl, silicone, vinyl-silicone, polyurethane, or a composite of aluminum oxide/boron nitride (AOBN), polyvinylidene fluoride, polyethylene, polypropylene, polydimethylsiloxane, perylene, polyamide, polytetrafluoroethylene, polymethylmethacrylate, polyimide, polyurethane, liquid crystalline polymers, nanocomposites, or the like. Openings 117A and 117B of insulation coating 116 may be formed by any suitable technique. In some examples, openings 117A and 117B are formed by a mechanical technique, such as, but not limited to, laser cutting, drilling, or punching. In other examples, openings 117A and 117B are formed by a chemical technique, such, but not limited to, the selective dissolution of one or more sections of the insulation coating 116, or any combination thereof. In some examples, there may be a 1 mm spacing between openings 117A and 117B, and "at distal end 118" includes examples where openings 117A and 117B are proximate to distal end 118.

Introducer needle 110 may operate in a unipolar configuration (e.g., a unipolar needle electrode) to stimulate a hypoglossal nerve and/or a motor point (e.g., one or more of motor points 54A, 54B, 55A, or 55B) in the tongue of a patient. For example, a surgeon may guide distal end 118 of elongated body 114 to a location proximal to the hypoglossal nerve and/or the motor point (e.g., one or more of motor points 54A, 54B, 55A, or 55B) and deliver stimulation signals through electrically conductive areas 112A and 112B of introducer needle 110 to the hypoglossal nerve and/or the motor point. In such cases, introducer needle 110 is coupled to a return electrode (e.g., a ground pad), where the return electrode is secured to the patient's skin. In some examples, electrically conductive areas 112A and 112B may be electrically isolated from another, and in such examples, one of electrically conductive areas 112A and 112B may be used to output the stimulation signals and the other of electrically conductive areas 112A and 112B may provide the return path.

The stimulation signals delivered to the hypoglossal nerve and/or the motor point (e.g., one or more of motor points 54A, 54B, 55A, or 55B) may cause a muscle contraction of a protrusor muscle, which may generate electrical signals. The electrical signals generated during the muscle contraction may be detected at electrically conductive areas 112A and 112B by introducer needle 110. The surgeon may control the medical device to receive the electrical signals and output information indicative of the one or more electrical signals on a display device. The surgeon may then determine a target treatment site based on the output information. In some examples, reception of electrical signals may not be necessary and visual inspection to determine if tongue 40 protruded or if protrusor muscles 42 and/or 46 activated may be sufficient.

In the example illustrated in FIG. 6C, after the target treatment site is determined, the surgeon may insert lead 90 in lumen 120 of introducer needle 110. As described in more detail, in some examples, rather than inserting lead 90 into lumen 120 of introducer needle 110, needle 110 may be removed and an introducer sheath is placed in the opening created by needle 110. Lead 90 is placed in the lumen of the introducer sheath.

As illustrated in FIG. 6C, electrodes 98A and 98B of lead 90 are aligned with electrically conductive areas 112A and 112B of the introducer needle 110 along a vertical axial A-A. The surgeon may then control the medical device to deliver a stimulation signal via electrodes 98A and 98B of lead 90 through electrically conductive areas 112A and 112B of the introducer needle 110 to the tongue of the patient to stimulate the hypoglossal nerve and/or the motor point (e.g., one or more of motor points 54A, 54B, 55A, or 55B) in the tongue of the patient. In this way, introducer needle 110 does not have to be withdrawn to expose electrodes 98A and 98B for testing to ensure that lead 90 is properly placed. In some examples, a first medical device may be used to provide stimulation to electrically conductive areas 112A, 112B and a second medical device may be used to provide stimulation to electrodes 98A and 98B after lead 90 is inserted into lumen 120. In some examples, the first medical device and the second medical device may be the same medical device.

Figure 7A:
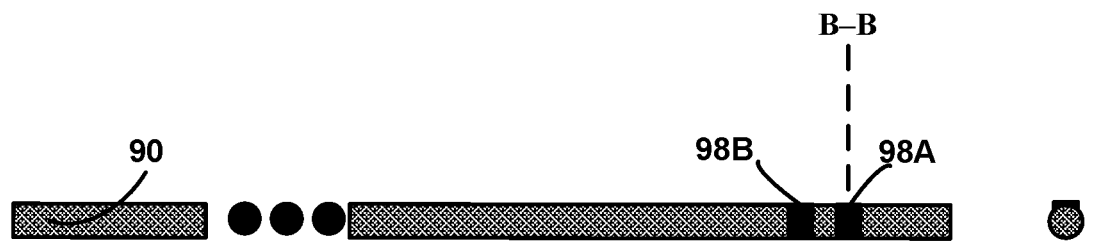
FIG. 7A-7C are conceptual diagrams illustrating the lead of FIG. 6A and another example introducer needle which may be utilized in the system of FIG. 1.
Figure 7B:
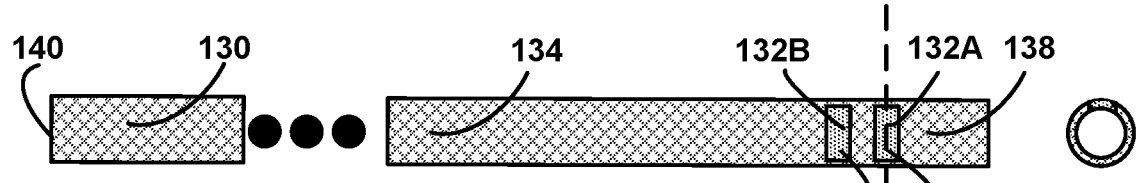
Figure 7C:
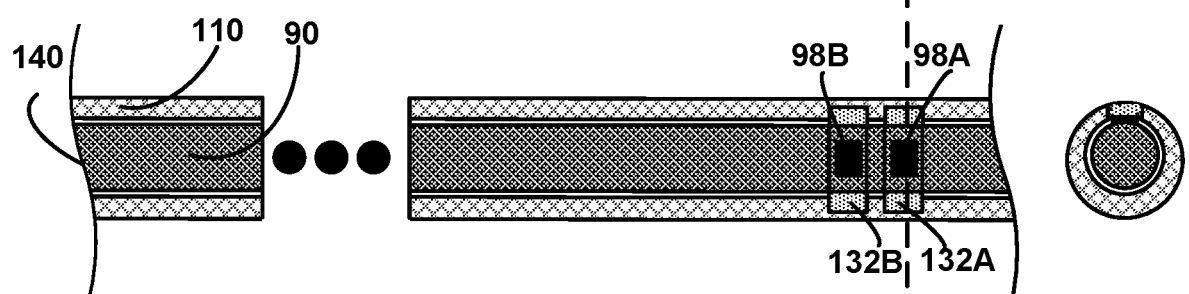

FIG. 7A-7C are conceptual diagrams illustrating the lead of FIG. 6A and another example introducer needle which may be utilized in the system of FIG. 1. Similar to FIG. 6A and reproduced for ease of understanding, FIG. 7A illustrates an example of lead 90 that includes electrodes 98A and 98B at a distal end of the lead. FIG. 7B illustrates an example of introducer needle 130 formed from a semiconducting material, where the introducer needle includes one or more electrode interfaces located at one or more electrically conductive areas. FIG. 7C illustrates the insertion of the lead in the introducer needle.

In the example illustrated in FIG. 7B, introducer needle 130 includes an elongated body 134 and electrode interfaces 136A and 136B. Elongated body 134 of introducer needle 130 is formed from any suitable semiconducting material, such as, but not limited to, germanium, selenium, silicon, or the like.

Electrode interfaces 136A and 136B are located at electrically conductive areas 112A and 112B at a distal end 138 of elongated body 134. In some examples, electrode interfaces 136A and 136B each include an electrode attached to the outer perimeter of elongated body 134 of introducer needle 130. In this way, introducer needle 130 may operate in a bipolar or multi-polar configuration with other electrode interfaces referenced to an electrode carried by the medical device (e.g., IMD 16). For example, one of electrode interfaces 136A and 136B may be used to deliver stimulation and the other one of electrode interfaces 136A and 136B may be used to provide a return path for the stimulation.

In the example illustrated in FIG. 7C, when lead 90 is inserted in lumen 140 of introducer needle 130, electrodes 98A and 98B of lead 90 are aligned with electrically conductive areas 132A and 132B of the introducer needle along a vertical axial B-B. After insertion of lead 90 in lumen 130 of introducer needle 130, the surgeon can control the medical device to deliver a stimulation signal via electrodes 98A and 98B of lead 90 through electrically conductive areas 132A and 132B of the introducer needle 130 to the tongue 40 of the patient to stimulate the hypoglossal nerve and/or the motor point (e.g., one or more of motor points 54A, 54B, 55A, or 55B). In this way, introducer needle 130 does not have to be withdrawn to expose electrodes 98A and 98B for testing to ensure that lead 90 is properly placed.

Figure 8A:
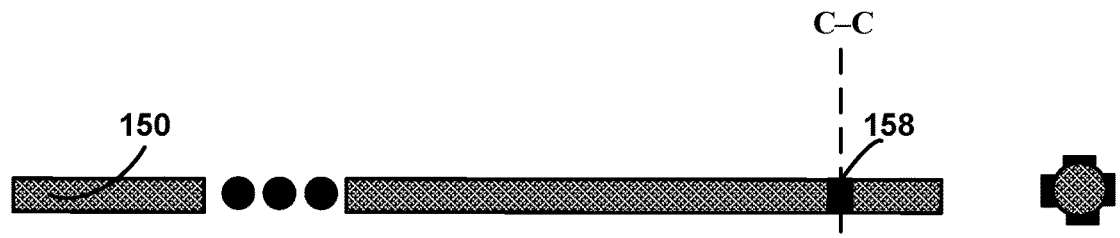
FIG. 8A-8D are conceptual diagrams illustrating another lead, another example introducer needle, and an example introducer sheath which may be utilized in the system of FIG. 1.
Figure 8B:
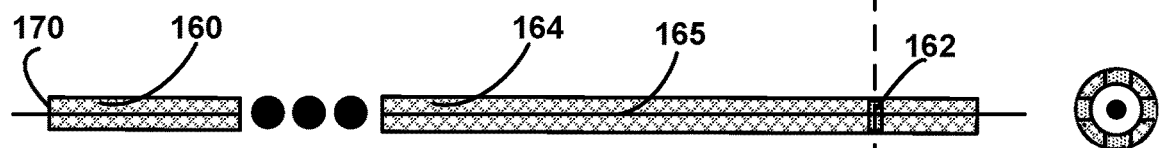
Figure 8C:
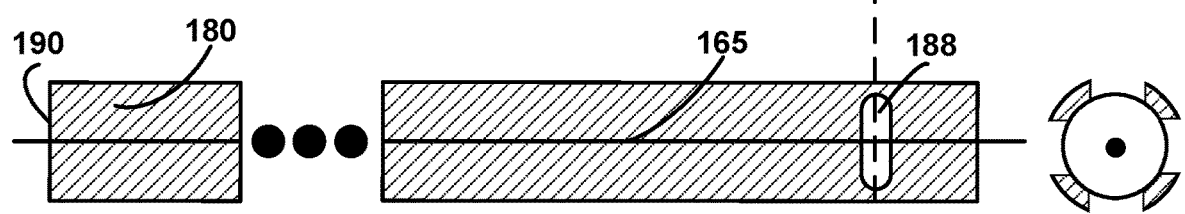
Figure 8D:
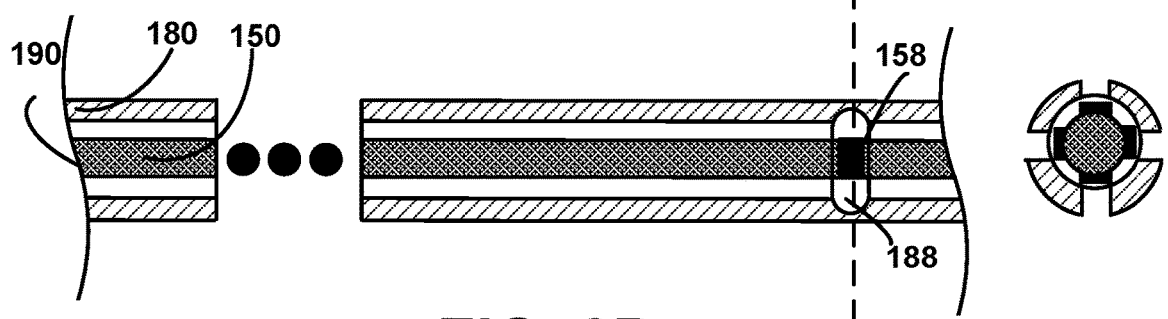

FIG. 8A-8D are conceptual diagrams illustrating another example lead 2, another example introducer needle, and an example introducer sheath which may be utilized in the system of FIG. 1. FIG. 8A illustrates an example of lead 150 that includes one or more electrodes 158 (for ease only electrode 158 is shown in FIG. 8A) at a distal end of the lead. FIG. 8B illustrates an example of introducer needle 160 that is similar to introducer needle 110 shown in FIG. 6B or introducer needle 130 shown in FIG. 7B. FIG. 8C illustrates an example of an introducer sheath 180 that includes perforations 188 (for ease only perforation 188 is shown in FIG. 8C) at a distal end of the introducer sheath. FIG. 8D illustrates the insertion of lead 150 in introducer sheath 180.

In some examples, lead 150 may have a relatively large diameter. For example, lead 150 may be a multi-polar lead that includes multiple electrodes attached to an outer perimeter of lead 150. For example, electrode 158 may include four electrodes circumstantially spaced from each other about the outer perimeter of lead 150.

There may be certain unique challenges associated with implanting a lead with a relatively large diameter. As an example, lead 150 may have a diameter equal to or larger than the diameter of introducer needle 160 so that lead 150 may not be inserted in lumen 170 of elongated body 164.

In some cases, rather than lead 150 being considered as having a large diameter, needle 160 may be considered as having a relatively small diameter. For instance, to minimize the size of the opening, needle 160 may be sized to have a relatively small diameter.

To place lead 150 within an opening created by introducer needle 160, a guidewire 165 and an introducer sheath 180 may be used to help insertion of lead 160 through tissue near a chin of a patient and through a tongue of the patient.

In the example illustrated in FIG. 8B, introducer needle 160 includes an elongated body 164 and one or more electrically conductive areas 162 (for ease only electrically conductive area 162 is shown in FIG. 8B) around a distal end of introducer needle 160. Elongated body 164 has a lumen 170 so that a surgeon may insert a guidewire 165 in lumen 170 of the elongated body. After guidewire 165 is placed in lumen 170 of elongated body 164, the surgeon may retract introducer needle 160 while leaving guidewire 165 in the tongue of the patient.

In the example illustrated in FIG. 8C, an introducer sheath 180 may be slide over guidewire 165 to reach a hypoglossal nerve and/or a motor point in the tongue of the patient.

Introducer sheath 180 is formed from any suitable material, such as, but not limited to, high density polyethylene, polytetrafluoroethylene, low-density polyethylene, or any combination thereof. Introducer sheath 180 includes a lumen 190, so that lead 150 may be inserted in lumen 190 of the introducer sheath.

Introducer sheath 180 further includes one or more perforations 188 (for ease only perforation 188 is shown in FIG. 8C) at a distal end 118 of Introducer sheath 180. In the examples illustrated in FIGS. 8B and 8C, perforation 188 of introducer sheath 180 is aligned with electrically conductive area 162 of introducer needle 160 along a vertical axial C-C.

Perforation 188 may be formed by any suitable technique. In some examples, perforation 188 is formed by a mechanical technique, such as, but not limited to, laser cutting, drilling, or punching. In other examples, perforation 188 is formed by a chemical technique, such, but not limited to, the selective dissolution of one or more sections of the introducer sheath 180, or any combination thereof.

In some examples, introducer sheath 180 may be coupled with a dilator to facilitate advancement of introducer sheath 180 into and through the opening created by introducer needle 160 so that introducer sheath 180 can be advanced along guidewire 165 to the hypoglossal nerve and/or the motor point (e.g., one or more of motor points 54A, 54B, 55A, or 55B). After guidewire 165 is placed in lumen 190 of introducer sheath 180, the surgeon may remove guidewire 165 and insert lead 150 in lumen 190 of introducer sheath 180.

In the example illustrated in FIG. 8D, perforation 188 of introducer sheath 180 is also aligned with electrode 158 of lead 150 along the vertical axial C-C. The surgeon may then control the medical device to deliver a stimulation signal via electrode 158 of lead 150 through perforations 188 of introducer sheath 180 to the tongue of the patient to stimulate the hypoglossal nerve and/or the motor point. In this way, lead 150 with a diameter equal to or larger than the diameter of introducer needle 160 may be advanced into and through the opening created by introducer needle 160.

Figure 9:
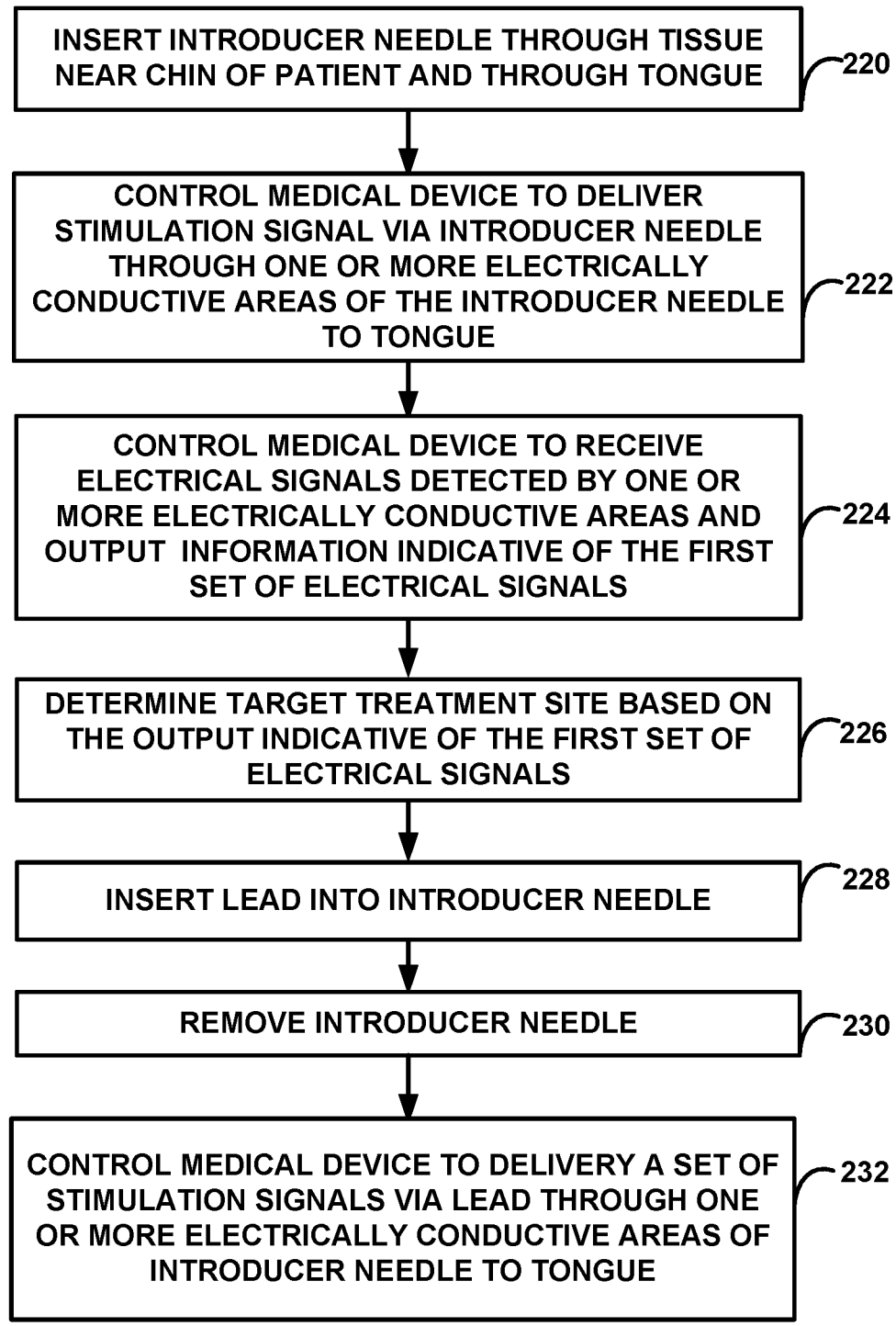
FIG. 9 is a flowchart illustrating an example of lead implantation.

FIG. 9 is a flowchart illustrating an example of lead implantation. A medical professional may insert an introducer needle (e.g., introducer needle 110, 130, or 160) through tissue near a chin of patient 14 and through tongue 40 of patient 14 (220). The introducer needle may include an elongated body having one or more electrically conductive areas for creating an opening in a tongue of a patient for implantation of a lead for treating OSA. The medical professional may control a medical device (e.g., IMD 16) to deliver a first stimulation signal via the introducer needle through the one or more electrically conductive areas to tongue 40 of patient 14 to stimulate a hypoglossal nerve and/or a motor (e.g., one or more of motor points 54A, 54B, 55A, or 55B) point (222).

In some examples, the medical professional may control the medical device to receive a first set of electrical signals detected by one or more of the electrically conductive areas of the introducer needle and output information indicative of the first set of electrical signals (224). The medical professional may then determine a target treatment site based on the output information indicative of the first set of electrical signals (226).

In some examples, the medical professional may insert a lead (e.g., lead 20 or lead 90) into the introducer needle (228), remove the introducer needle (230), and control the medical device to deliver a first set of stimulation signals via the lead through the one or more electrically conductive areas of the introducer needle to the tongue of the patient to stimulate the hypoglossal nerve and/or the motor point (e.g., one or more of motor points 54A, 54B, 55A, or 55B) in the tongue of the patient (232). As described above, one or more electrodes of the lead align with the one or more electrically conductive areas of the introducer needle. For example, electrodes 98A and 98B of lead 90 align with electrically conductive areas 112A and 112B of introducer needle 110.

Figure 10:
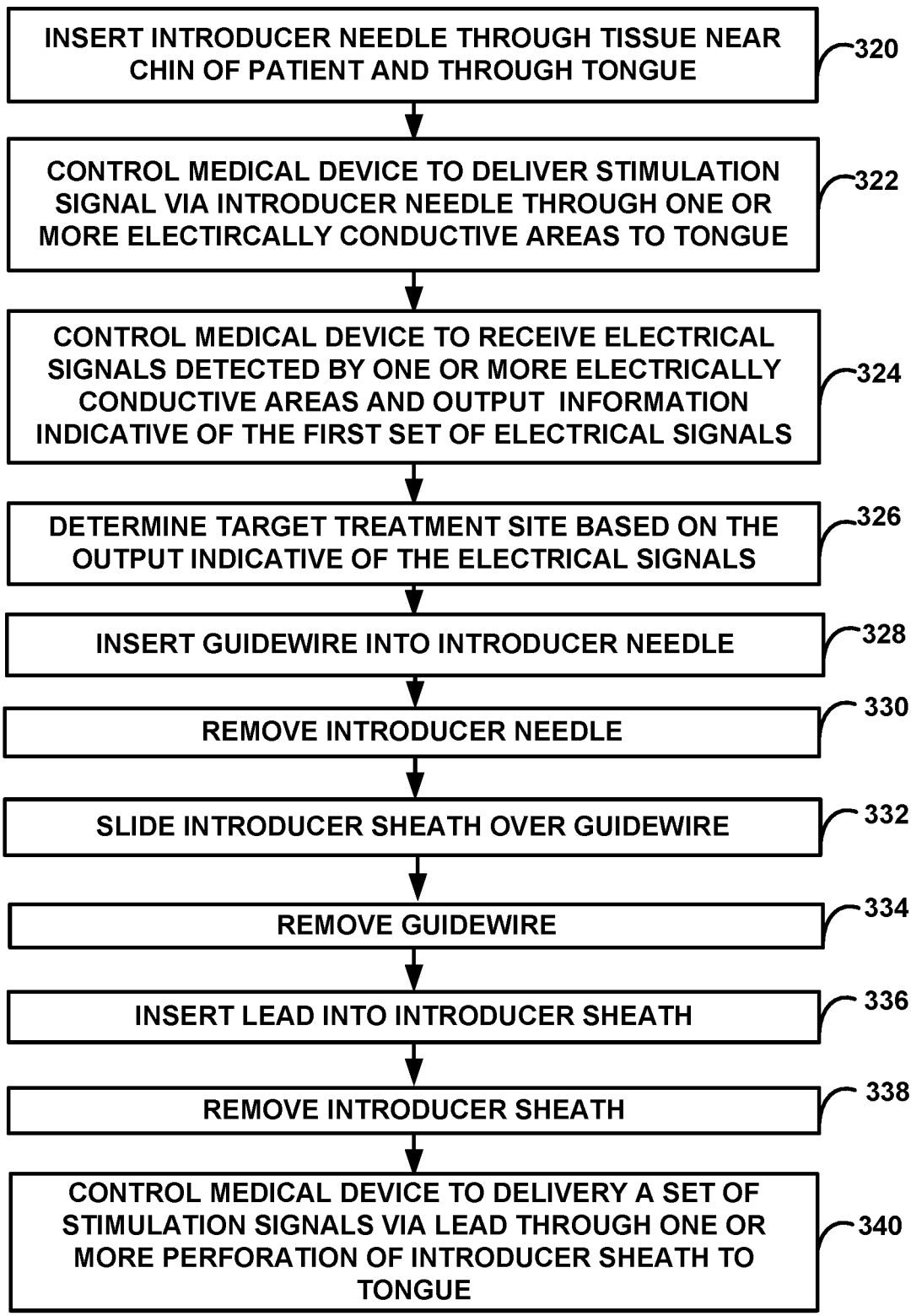
FIG. 10 is a flowchart illustrating another example of lead implantation.

FIG. 10 is another flowchart illustrating an example of lead implantation. A medical professional may insert an introducer needle (e.g., introducer needle 110, 130, or 160) through tissue near a chin of patient 14 and through tongue 40 of patient 14 (320). The introducer needle may include an elongated body having one or more electrically conductive areas for creating an opening in a tongue of a patient for implantation of a lead for treating OSA. The medical professional may control a first medical device (e.g., IMD 16) to deliver a first stimulation signal via the introducer needle through the one or more electrically conductive areas to tongue 40 of patient 14 to stimulate a hypoglossal nerve and/or a motor point (e.g., one or more of motor points 54A, 54B, 55A, or 55B) (322).

In some examples, the medical professional may control the first medical device to receive a first set of electrical signals detected by one or more of the electrically conductive areas of the introducer needle and output information indicative of the first set of electrical signals (324). The medical professional may then determine a target treatment site based on the output information indicative of the first set of electrical signals (326).

In some examples, the medical professional may insert a guidewire (e.g., guidewire 165) into the introducer needle (328), remove the introducer needle (330), slide an introducer sheath (e.g., introducer sheath 180) over the guidewire (332), and remove the guidewire (334).

In some examples, the medical professional may insert a lead (e.g., lead 20, 90, or 150) into the introducer sheath (336), remove the introducer sheath (338), and control a second medical device to deliver a second set of stimulation signals via the lead through the one or more electrically conductive areas of the introducer needle to the tongue of the patient to stimulate the hypoglossal nerve and/or the motor point (e.g., one or more of motor points 54A, 54B, 55A, or 55B) in the tongue of the patient (340). As described above, in some examples, the first medical device and the second medical device may be different medical devices. In other examples, the first medical device and the second medical device may be the same medical device. One or more perforations of the introducer sheath are aligned with the one or more electrically conductive areas of the introducer needle. For example, perforation 188 of introducer sheath 180 is aligned with electrically conductive area 162 of introducer needle 160. The one or more perforations of the introducer sheath are further aligned with the one or more electrodes of the lead. For example, perforation 188 of introducer sheath 180 is aligned with electrode 158 of lead 150.

It should be noted that system 10, and the techniques described herein, may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure. Various examples are described herein, such as the following examples.

Example 1. A system for treatment of obstructive sleep apnea (OSA), the system comprising: an introducer needle comprising an elongated body having one or more electrically conductive areas for creating an opening in a tongue of a patient for implantation of a lead for treating OSA; and a medical device configured to deliver a stimulation signal via the introducer needle through the one or more electrically conductive areas to the tongue of the patient to stimulate one or more motor points of a protrusor muscle within the tongue of the patient.

Example 2. The system of example 1, wherein the medical device is configured to receive one or more electrical signals detected by the one or more of the electrically conductive areas of the introducer needle and output information indicative of the one or more electrical signals.

Example 3. The system of example 2, wherein the one or more electrical signals include an electromyography (EMG) signal.

Example 4. The system of any of examples 1-3, wherein the one or more electrically conductive areas are located at a distal end of the introducer needle.

Example 5. The system of any of examples 1-4, wherein the one or more electrically conductive areas comprises less than four electrically conductive areas.

Example 6. The system of any of examples 1-5, wherein the introducer needle is formed from a semiconducting material, the introducer needle comprises one or more electrode interfaces, wherein the one or more electrode interfaces are located at the one or more electrically conductive areas.

Example 7. The system of any of examples 1-5, wherein the introducer needle is formed from a conducting material, the introducer needle comprises an insulation coating, wherein the insulation coating defines the one or more electrically conductive areas.

Example 8. The system of any of examples 1-7, wherein one or more electrodes of the lead are aligned with the one or more electrically conductive areas of the introducer needle.

Example 9. The system of any of examples 1-8, the medical device is further configured to deliver a first set of stimulation signals via one or more electrodes of the lead through the one or more electrically conductive areas of the introducer needle to the tongue of the patient to stimulate the one or more motor points of the protrusor muscle within the tongue of the patient.

Example 10. The system of any of examples 1-9, further comprising: an introducer sheath, wherein the introducer sheath is configured to be placed within the opening created by the introducer needle, wherein the introducer sheath comprises one or more perforations.

Example 11. The system of example 10, wherein the one or more perforations of the introducer sheath align with the one or more electrically conductive areas of the introducer needle.

Example 12. The system of any of examples 10-11, wherein the one or more perforations of the introducer sheath align with the one or more electrodes of the lead.

Example 13. The system of any of examples 10-12, the medical device is further configured to deliver a second set of stimulation signals via the one or more electrodes of the lead through the one or more perforations of the introducer sheath to the tongue of the patient to stimulate the one or more motor points of the protrusor muscle within the tongue of the patient.

Example 14. A system for treatment of obstructive sleep apnea (OSA), the system comprising: an introducer needle comprising an elongated body having one or more electrically conductive areas for creating an opening in a tongue of a patient for implantation of a lead for treating OSA; an introducer sheath configured to be placed within the opening created by the introducer needle, wherein the introducer sheath comprises one or more perforations that align with one or more electrodes of a lead inserted into the introducer sheath; and one or more medical devices are configured to deliver a stimulation signal via the introducer needle through the one or more electrically conductive areas to the tongue of the patient to stimulate one or more motor points of a protrusor muscle within the tongue of the patient, wherein the one or more medical devices are further configured to deliver the stimulation signal with the one or more electrodes of the lead that is inserted into the introducer sheath and through the one or more perforations of the introducer sheath to the tongue of the patient.

Example 15. The system of example 14, wherein the one or more medical devices are configured to receive one or more electrical signals detected by the one or more of the electrically conductive areas of the introducer needle and output information indicative of the one or more electrical signals.

Example 16. The system of example 15, wherein the one or more electrical signals include an electromyography (EMG) signal.

Example 17. The system of any of examples 14-16, wherein the one or more electrically conductive areas are located at a distal end of the introducer needle.

Example 18. The system of any of examples 14-17, wherein the one or more electrically conductive areas comprises less than four electrically conductive areas.

Example 19. The system of any of examples 14-18, wherein the introducer needle is formed from a semiconducting material, the introducer needle comprises one or more electrode interfaces, wherein the one or more electrode interfaces are located at the one or more electrically conductive areas.

Example 20. The system of any of examples 14-18, wherein the introducer needle is formed from a conducting material, the introducer needle comprises an insulation coating, wherein the insulation coating defines the one or more electrically conductive areas.

Example 21. The system of any of examples 14-20, wherein one or more electrodes of the lead are aligned with the one or more electrically conductive areas of the introducer needle.

Example 22. The system of any of examples 14-11, wherein the one or more perforations of the introducer sheath align with one or more electrodes of the lead.

Example 23. A method for treatment of obstructive sleep apnea (OSA), the method comprising: inserting an introducer needle through tissue near a chin of a patient and through a tongue of the patient, wherein the introducer needle comprises an elongated body having one or more electrically conductive areas, wherein the introducer needle is for creating an opening in the tongue of the patient for implantation of a lead for treating OSA; and controlling a medical device to deliver a stimulation signal via the introducer needle through the one or more electrically conductive areas to the tongue of the patient to stimulate one or more motor points of a protrusor muscle within the tongue of the patient.

Example 24. The method of example 23, further comprising: inserting the lead into the introducer needle, wherein the one or more electrodes of the lead align with the one or more electrically conductive areas of the introducer needle; removing the introducer needle; and controlling the medical device to deliver a first set of stimulation signals via the lead through the one or more electrically conductive areas of the introducer needle to the tongue of the patient to stimulate the one or more motor points of the protrusor muscle within the tongue of the patient.

Example 25. The method of any of examples 23 and 24, further comprising: inserting the lead into an introducer sheath, wherein the introducer sheath comprises one or more perforations, wherein the one or more perforations align with the one or more electrically conductive areas of the introducer needle, wherein the one or more perforations of the introducer sheath align with the one or more electrodes of the lead; removing the introducer sheath; and controlling the medical device to deliver a second set of stimulation signals via the lead through the one or more perforations of the introducer sheath to the tongue of the patient to stimulate the one or more motor points of the protrusor muscle within the tongue of the patient.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method for treatment of obstructive sleep apnea (OSA), the method comprising:
    inserting an introducer needle through tissue near a chin of a patient and through a tongue of the patient, wherein the introducer needle comprises an elongated body having one or more electrically conductive areas, wherein the introducer needle is for creating an opening in the tongue of the patient for implantation of a lead having one or more electrodes for treating OSA, the one or more electrodes of the lead i) align with the one or more electrically conductive areas of the introducer needle when the lead is inserted into the introducer needle; or ii) align with one or more perforations of an introducer sheath when the lead is inserted into the introducer sheath; and
    controlling a medical device to deliver a stimulation signal via the introducer needle through the one or more electrically conductive areas to the tongue of the patient to stimulate one or more motor points of a protrusor muscle within the tongue of the patient.

2. The method of claim 1,
    wherein inserting the lead into at least one of the introducer needle or the introducer sheath comprises inserting the lead into the introducer needle, the method further comprising:
    controlling the medical device to deliver a set of stimulation signals via the lead through the one or more electrically conductive areas of the introducer needle to the tongue of the patient to stimulate the one or more motor points of the protrusor muscle within the tongue of the patient; and
    removing the introducer needle.

3. The method of claim 1,
    wherein inserting the lead into at least one of the introducer needle or the introducer sheath comprises inserting the lead into an introducer sheath
    wherein the one or more perforations of the introducer sheath align with the one or more electrically conductive areas of the introducer needle, the method further comprising:
    controlling the medical device to deliver a set of stimulation signals via the lead through the one or more perforations of the introducer sheath to the tongue of the patient to stimulate the one or more motor points of the protrusor muscle within the tongue of the patient; and
    removing the introducer sheath.

* * * * *